US008517931B2

(12) United States Patent  
Minnelli et al.

(10) Patent No.: US 8,517,931 B2  
(45) Date of Patent: Aug. 27, 2013

(54) TISSUE RETRACTORS

(75) Inventors: Patrick J. Minnelli, Harrison, OH (US); Gregory W. Johnson, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1671 days.

(21) Appl. No.: 11/944,806

(22) Filed: Nov. 26, 2007

(65) Prior Publication Data

US 2009/0137877 A1    May 28, 2009

(51) Int. Cl.
*A61B 1/32* (2006.01)

(52) U.S. Cl.
USPC .......................................................... 600/201

(58) Field of Classification Search
USPC ................ 600/184, 201, 203, 206, 208–210, 600/235; 128/830–834, 837; 623/1.5, 1.51, 623/2.14, 2.18, 23.72, 23.74, 23.76; 606/151, 606/167, 179, 185, 232, 228
See application file for complete search history.

(56) References Cited

U.S. PATENT DOCUMENTS

| | | | |
|---|---|---|---|
| 4,693,720 A * | 9/1987 | Scharnberg et al. | ....... 623/23.72 |
| RE32,922 E | 5/1989 | Levin et al. | |
| 4,984,564 A | 1/1991 | Yuen | |
| RE33,585 E | 5/1991 | Haber et al. | |
| 5,062,847 A | 11/1991 | Barnes | |
| 5,152,279 A | 10/1992 | Wilk | |
| 5,163,942 A | 11/1992 | Rydell | |
| 5,178,133 A | 1/1993 | Pena | |
| 5,195,505 A | 3/1993 | Josefsen | |
| 5,195,506 A | 3/1993 | Hulfish | |
| 5,267,554 A | 12/1993 | Wilk | |
| 5,271,385 A | 12/1993 | Bailey | |
| 5,273,026 A | 12/1993 | Wilk | |
| 5,280,782 A | 1/1994 | Wilk | |
| 5,301,658 A | 4/1994 | Zhu et al. | |
| 5,309,896 A | 5/1994 | Moll et al. | |
| 5,318,586 A | 6/1994 | Ereren | |
| 5,333,624 A * | 8/1994 | Tovey | .......................... 128/897 |
| 5,337,736 A | 8/1994 | Reddy | |
| 5,339,801 A | 8/1994 | Poloyko et al. | |
| 5,352,237 A | 10/1994 | Rodak et al. | |

(Continued)

FOREIGN PATENT DOCUMENTS

| | | |
|---|---|---|
| EP | 288879 A2 | 11/1988 |
| EP | 353916 A1 | 2/1990 |

(Continued)

OTHER PUBLICATIONS

International Search Report & Written Opinion, PCT/US2008/084475, Mailed Jun. 30, 2009, 15 pages.

(Continued)

*Primary Examiner* — Anu Ramana
(74) *Attorney, Agent, or Firm* — Nutter McClennen & Fish LLP

(57) ABSTRACT

Methods and devices are provided for performing surgical procedures using tissue retractors. In general, a surgical retractor device is provided that includes a flexible fabric tissue retractor configured to support tissue. At least one grasping element can be coupled to a perimeter of the flexible fabric, and the grasping elements can be manipulated to couple the flexible fabric to a surgical port, e.g., a trocar, inserted through a body wall and extending into a body cavity. The grasping element can also be configured to move the flexible fabric and thereby move the tissue.

18 Claims, 16 Drawing Sheets

(56) References Cited

U.S. PATENT DOCUMENTS

| | | | |
|---|---|---|---|
| 5,353,784 A | 10/1994 | Nady-Mohamed | |
| 5,359,995 A | 11/1994 | Sewell, Jr. | |
| 5,361,752 A | 11/1994 | Moll et al. | |
| 5,362,294 A | 11/1994 | Seitzinger | |
| 5,366,460 A * | 11/1994 | Eberbach | 606/151 |
| 5,381,788 A | 1/1995 | Matula et al. | |
| 5,391,180 A | 2/1995 | Tovey et al. | |
| 5,400,773 A | 3/1995 | Zhu et al. | |
| 5,402,772 A | 4/1995 | Moll et al. | |
| 5,415,666 A | 5/1995 | Gourlay et al. | |
| 5,425,357 A | 6/1995 | Moll et al. | |
| 5,439,476 A | 8/1995 | Frantzides | |
| 5,441,044 A | 8/1995 | Tovey et al. | |
| 5,450,843 A | 9/1995 | Moll et al. | |
| 5,454,367 A | 10/1995 | Moll et al. | |
| 5,465,711 A | 11/1995 | Moll et al. | |
| 5,468,248 A | 11/1995 | Chin et al. | |
| 5,512,037 A | 4/1996 | Russell et al. | |
| 5,514,075 A | 5/1996 | Moll et al. | |
| 5,514,157 A | 5/1996 | Nicholas et al. | |
| 5,527,264 A | 6/1996 | Moll et al. | |
| RE35,312 E | 8/1996 | Christoudias | |
| 5,549,636 A | 8/1996 | Li | |
| 5,554,101 A | 9/1996 | Matula et al. | |
| 5,562,603 A | 10/1996 | Moll et al. | |
| 5,569,165 A | 10/1996 | Chin et al. | |
| 5,575,759 A | 11/1996 | Moll et al. | |
| 5,582,577 A | 12/1996 | Lund et al. | |
| 5,588,951 A | 12/1996 | Zhu et al. | |
| 5,591,182 A | 1/1997 | Johnson | |
| 5,690,607 A | 11/1997 | Chin et al. | |
| 5,716,327 A | 2/1998 | Warner et al. | |
| 5,722,935 A | 3/1998 | Christian | |
| 5,738,629 A | 4/1998 | Moll et al. | |
| 5,743,851 A | 4/1998 | Moll et al. | |
| 5,755,661 A | 5/1998 | Schwartzman | |
| 5,772,680 A | 6/1998 | Kieturakis et al. | |
| 5,803,902 A | 9/1998 | Sienkiewicz et al. | |
| 5,823,945 A | 10/1998 | Moll et al. | |
| 5,860,987 A | 1/1999 | Ratcliff et al. | |
| 5,865,728 A | 2/1999 | Moll et al. | |
| 5,865,802 A | 2/1999 | Yoon et al. | |
| 5,885,271 A | 3/1999 | Hamilton et al. | |
| 5,906,205 A | 5/1999 | Hiebert | |
| 5,924,424 A * | 7/1999 | Stevens et al. | 128/898 |
| 5,954,767 A * | 9/1999 | Pajotin et al. | 623/23.72 |
| 6,036,640 A | 3/2000 | Corace et al. | |
| 6,056,768 A | 5/2000 | Cates et al. | |
| 6,063,112 A | 5/2000 | Sgro et al. | |
| 6,090,042 A | 7/2000 | Rullo et al. | |
| 6,146,401 A | 11/2000 | Yoon et al. | |
| 6,159,201 A | 12/2000 | Hamilton et al. | |
| 6,162,172 A | 12/2000 | Cosgrove et al. | |
| 6,179,852 B1 | 1/2001 | Strickland et al. | |
| 6,190,311 B1 | 2/2001 | Glines et al. | |
| 6,199,556 B1 | 3/2001 | Benetti et al. | |
| 6,214,020 B1 * | 4/2001 | Mulhauser et al. | 606/151 |
| 6,248,062 B1 | 6/2001 | Adler et al. | |
| 6,248,119 B1 | 6/2001 | Solem et al. | |
| 6,309,349 B1 | 10/2001 | Bertolero et al. | |
| 6,361,543 B1 | 3/2002 | Chin et al. | |
| 6,371,964 B1 | 4/2002 | Vargas et al. | |
| 6,478,029 B1 | 11/2002 | Boyd et al. | |
| 6,508,252 B1 | 1/2003 | Berg et al. | |
| 6,508,826 B2 | 1/2003 | Murphy et al. | |
| 6,517,563 B1 | 2/2003 | Paolitto et al. | |
| 6,592,515 B2 | 7/2003 | Thierfelder et al. | |
| 6,605,037 B1 | 8/2003 | Moll et al. | |
| 6,613,055 B2 | 9/2003 | Di Emidio et al. | |
| 6,656,109 B2 | 12/2003 | DeVries et al. | |
| 6,663,562 B2 | 12/2003 | Chang | |
| 6,666,846 B1 | 12/2003 | Turovskiy et al. | |
| 6,689,103 B1 | 2/2004 | Palasis | |
| 6,712,795 B1 | 3/2004 | Cohen | |
| 6,786,898 B2 | 9/2004 | Guenst | |
| 6,830,546 B1 | 12/2004 | Chin et al. | |
| 6,890,295 B2 | 5/2005 | Michels et al. | |
| 6,936,005 B2 | 8/2005 | Poff et al. | |
| 6,986,774 B2 | 1/2006 | Middleman et al. | |
| 7,004,970 B2 * | 2/2006 | Cauthen, III et al. | 623/17.16 |
| 7,063,693 B2 | 6/2006 | Guenst | |
| 7,112,172 B2 | 9/2006 | Orban, III et al. | |
| 7,122,003 B2 | 10/2006 | Nakao | |
| 7,341,601 B2 * | 3/2008 | Eisermann et al. | 623/17.11 |
| 7,404,819 B1 * | 7/2008 | Darios et al. | 606/151 |
| 7,833,284 B2 * | 11/2010 | Lieberman | 623/23.74 |
| 2001/0009987 A1 | 7/2001 | Moshe et al. | |
| 2001/0034527 A1 | 10/2001 | Scribner et al. | |
| 2001/0037053 A1 | 11/2001 | Bonadio et al. | |
| 2001/0051822 A1 | 12/2001 | Stack et al. | |
| 2002/0010388 A1 | 1/2002 | Taylor et al. | |
| 2002/0010389 A1 | 1/2002 | Butler et al. | |
| 2002/0022770 A1 | 2/2002 | Borsody | |
| 2002/0022845 A1 | 2/2002 | Zdeblick et al. | |
| 2002/0038128 A1 | 3/2002 | Turovkiy et al. | |
| 2002/0056460 A1 | 5/2002 | Boyd et al. | |
| 2002/0068923 A1 | 6/2002 | Caldwell et al. | |
| 2002/0069884 A1 | 6/2002 | Boyd et al. | |
| 2002/0074004 A1 | 6/2002 | Boyd et al. | |
| 2002/0077637 A1 | 6/2002 | Vargas et al. | |
| 2002/0087183 A1 | 7/2002 | Boyd et al. | |
| 2002/0091354 A1 | 7/2002 | Navia et al. | |
| 2002/0092533 A1 | 7/2002 | Boyd et al. | |
| 2002/0099270 A1 | 7/2002 | Taylor et al. | |
| 2002/0099338 A1 | 7/2002 | Young | |
| 2002/0099447 A1 | 7/2002 | Mears et al. | |
| 2002/0143343 A1 | 10/2002 | Castro | |
| 2002/0151902 A1 | 10/2002 | Riedel et al. | |
| 2002/0161391 A1 | 10/2002 | Murphy et al. | |
| 2002/0162559 A1 | 11/2002 | Crook | |
| 2002/0177874 A1 | 11/2002 | Nicholas et al. | |
| 2002/0183594 A1 | 12/2002 | Beane et al. | |
| 2002/0188301 A1 | 12/2002 | Dallara et al. | |
| 2002/0193863 A1 | 12/2002 | Rourke et al. | |
| 2003/0032967 A1 | 2/2003 | Park et al. | |
| 2003/0040717 A1 | 2/2003 | Saulenas et al. | |
| 2003/0055319 A1 | 3/2003 | Chang | |
| 2003/0062051 A1 | 4/2003 | Rambo | |
| 2003/0065351 A1 | 4/2003 | Hess et al. | |
| 2003/0074015 A1 | 4/2003 | Nakao | |
| 2003/0078478 A1 | 4/2003 | Bonadio et al. | |
| 2003/0083621 A1 | 5/2003 | Shaw et al. | |
| 2003/0105486 A1 | 6/2003 | Murphy et al. | |
| 2003/0176771 A1 | 9/2003 | Pulford et al. | |
| 2003/0187376 A1 | 10/2003 | Rambo | |
| 2003/0191478 A1 | 10/2003 | Kortenbach et al. | |
| 2003/0192553 A1 | 10/2003 | Rambo | |
| 2003/0195519 A1 | 10/2003 | Zdeblick et al. | |
| 2003/0195544 A1 | 10/2003 | Hess et al. | |
| 2004/0034351 A1 | 2/2004 | Sherman et al. | |
| 2004/0049100 A1 | 3/2004 | Butler et al. | |
| 2004/0068276 A1 | 4/2004 | Golden et al. | |
| 2004/0073090 A1 | 4/2004 | Butler et al. | |
| 2004/0082923 A1 | 4/2004 | Field | |
| 2004/0092796 A1 | 5/2004 | Butler et al. | |
| 2004/0097793 A1 | 5/2004 | Butler et al. | |
| 2004/0097949 A1 | 5/2004 | Bonutti | |
| 2004/0133222 A1 | 7/2004 | Tran et al. | |
| 2004/0138526 A1 | 7/2004 | Guenst | |
| 2004/0143167 A1 | 7/2004 | Branch et al. | |
| 2004/0147812 A1 | 7/2004 | Hamel | |
| 2004/0176665 A1 | 9/2004 | Branch et al. | |
| 2004/0199052 A1 | 10/2004 | Banik et al. | |
| 2004/0254426 A1 | 12/2004 | Wenchell | |
| 2004/0260153 A1 | 12/2004 | Pulford et al. | |
| 2004/0267303 A1 | 12/2004 | Guenst | |
| 2005/0080435 A1 | 4/2005 | Smith et al. | |
| 2005/0119640 A1 | 6/2005 | Sverduk et al. | |
| 2005/0131391 A1 | 6/2005 | Chu et al. | |
| 2005/0165449 A1 | 7/2005 | Cadeddu et al. | |
| 2005/0192483 A1 | 9/2005 | Bonadio et al. | |
| 2005/0203344 A1 | 9/2005 | Orban et al. | |
| 2005/0240209 A1 | 10/2005 | Hamada | |
| 2005/0245945 A1 | 11/2005 | Ewers et al. | |

| Publication No. | Date | Inventor |
|---|---|---|
| 2005/0267336 A1 | 12/2005 | Bertolero et al. |
| 2005/0273129 A1 | 12/2005 | Michels et al. |
| 2006/0030884 A1 | 2/2006 | Yeung et al. |
| 2006/0036277 A1 | 2/2006 | Kieturakis et al. |
| 2006/0052799 A1 | 3/2006 | Middleman et al. |
| 2006/0106288 A1 | 5/2006 | Roth et al. |
| 2006/0122462 A1 | 6/2006 | Roth et al. |
| 2006/0151568 A1 | 7/2006 | Weller et al. |
| 2006/0189889 A1 | 8/2006 | Gertner |
| 2006/0200002 A1 | 9/2006 | Guenst |
| 2006/0247678 A1 | 11/2006 | Weisenburgh et al. |
| 2006/0248678 A1 | 11/2006 | Park |
| 2006/0258899 A1 | 11/2006 | Gill et al. |
| 2006/0270911 A1 | 11/2006 | Voegele et al. |
| 2009/0062618 A1 | 3/2009 | Drew et al. |

FOREIGN PATENT DOCUMENTS

| | | |
|---|---|---|
| EP | 410561 A1 | 1/1991 |
| EP | 449663 | 10/1991 |
| EP | 469524 A1 | 2/1992 |
| EP | 499457 A1 | 8/1992 |
| EP | 545540 A1 | 6/1993 |
| EP | 568296 A1 | 11/1993 |
| EP | 586516 A1 | 3/1994 |
| EP | 586555 A1 | 3/1994 |
| EP | 602757 A2 | 6/1994 |
| EP | 610099 | 8/1994 |
| EP | 613351 A1 | 9/1994 |
| EP | 613659 A1 | 9/1994 |
| EP | 630211 A1 | 12/1994 |
| EP | 636036 A1 | 2/1995 |
| EP | 654247 A1 | 5/1995 |
| EP | 698374 A2 | 2/1996 |
| EP | 720446 A1 | 7/1996 |
| EP | 734231 A1 | 10/1996 |
| EP | 746350 A1 | 12/1996 |
| EP | 786961 | 8/1997 |
| EP | 791330 A2 | 8/1997 |
| EP | 810843 A1 | 12/1997 |
| EP | 835639 A2 | 4/1998 |
| EP | 843987 A1 | 5/1998 |
| EP | 875260 A2 | 11/1998 |
| EP | 888750 A1 | 1/1999 |
| EP | 906064 A1 | 4/1999 |
| EP | 956060 A1 | 11/1999 |
| EP | 981302 A1 | 3/2000 |
| EP | 983024 | 3/2000 |
| EP | 1125552 A1 | 8/2001 |
| EP | 1171040 | 1/2002 |
| EP | 1177772 A1 | 2/2002 |
| EP | 1208865 A2 | 5/2002 |
| EP | 1312318 A1 | 5/2003 |
| EP | 1472982 A2 | 11/2004 |
| EP | 1498079 | 1/2005 |
| EP | 1698272 | 9/2006 |
| EP | 1698293 | 9/2006 |
| WO | WO-9106261 A1 | 5/1991 |
| WO | WO-9211811 | 7/1992 |
| WO | WO-9219294 A1 | 11/1992 |
| WO | WO-9221292 A2 | 12/1992 |
| WO | WO-9221294 A1 | 12/1992 |
| WO | WO-9309709 | 5/1993 |
| WO | WO-9309722 A1 | 5/1993 |
| WO | WO-9311811 A1 | 6/1993 |
| WO | WO-9317625 A1 | 9/1993 |
| WO | WO-9320755 A1 | 10/1993 |
| WO | WO-9320866 A1 | 10/1993 |
| WO | WO-9322973 A1 | 11/1993 |
| WO | WO-9325148 A1 | 12/1993 |
| WO | WO-9403114 A1 | 2/1994 |
| WO | WO-9416630 A1 | 8/1994 |
| WO | WO-9422384 A1 | 10/1994 |
| WO | WO-9424947 A1 | 11/1994 |
| WO | WO-9501193 A1 | 1/1995 |
| WO | WO-9502988 A2 | 2/1995 |
| WO | WO-9508952 A1 | 4/1995 |
| WO | WO-9515723 A1 | 6/1995 |
| WO | WO-9522289 A2 | 8/1995 |
| WO | WO-9602195 A1 | 2/1996 |
| WO | WO-9610430 A2 | 4/1996 |
| WO | WO-9620749 A1 | 7/1996 |
| WO | WO-9624291 A1 | 8/1996 |
| WO | WO-9640354 A1 | 12/1996 |
| WO | WO-9700049 A1 | 1/1997 |
| WO | WO-9707741 A1 | 3/1997 |
| WO | WO-9707742 A1 | 3/1997 |
| WO | WO-9725940 A1 | 7/1997 |
| WO | WO-9730666 A2 | 8/1997 |
| WO | WO-9732514 A2 | 9/1997 |
| WO | WO-9742893 A1 | 11/1997 |
| WO | WO-9802102 A2 | 1/1998 |
| WO | WO-9817208 A2 | 4/1998 |
| WO | WO-9824374 A1 | 6/1998 |
| WO | WO-9827869 A1 | 7/1998 |
| WO | WO-9834569 A1 | 8/1998 |
| WO | WO-9835714 A1 | 8/1998 |
| WO | WO-9848724 A1 | 11/1998 |
| WO | WO-9855029 A1 | 12/1998 |
| WO | WO-9903416 A1 | 1/1999 |
| WO | WO-9905976 A1 | 2/1999 |
| WO | WO-9909892 A1 | 3/1999 |
| WO | WO-9912477 A1 | 3/1999 |
| WO | WO-9912481 A1 | 3/1999 |
| WO | WO-9915226 A1 | 4/1999 |
| WO | WO-9921484 A2 | 5/1999 |
| WO | WO-9937345 A1 | 7/1999 |
| WO | WO-9938440 A1 | 8/1999 |
| WO | WO-9952445 A1 | 10/1999 |
| WO | WO-9952448 A1 | 10/1999 |
| WO | WO-9962457 A1 | 12/1999 |
| WO | WO-0001293 A2 | 1/2000 |
| WO | WO-0009024 A1 | 2/2000 |
| WO | WO-0010466 A1 | 3/2000 |
| WO | WO-0024326 A2 | 5/2000 |
| WO | WO-0032116 A1 | 6/2000 |
| WO | WO-0054675 A1 | 9/2000 |
| WO | WO-0061011 A1 | 10/2000 |
| WO | WO-0061035 A1 | 10/2000 |
| WO | WO-0062845 A1 | 10/2000 |
| WO | WO-0069346 A1 | 11/2000 |
| WO | WO-0069368 A2 | 11/2000 |
| WO | WO-0071033 A1 | 11/2000 |
| WO | WO-0078246 A2 | 12/2000 |
| WO | WO-0108581 A2 | 2/2001 |
| WO | WO-0124682 A2 | 4/2001 |
| WO | WO-0126558 A1 | 4/2001 |
| WO | WO-0126559 A1 | 4/2001 |
| WO | WO-0134228 A1 | 5/2001 |
| WO | WO-0160262 A1 | 8/2001 |
| WO | WO-0209591 A2 | 2/2002 |
| WO | WO-0222053 A2 | 3/2002 |
| WO | WO-0239880 A2 | 5/2002 |
| WO | WO-02058993 A1 | 8/2002 |
| WO | WO-02076308 A2 | 10/2002 |
| WO | WO-02087652 A2 | 11/2002 |
| WO | WO-03000142 A2 | 1/2003 |
| WO | WO-03015855 A1 | 2/2003 |
| WO | WO-03028523 A2 | 4/2003 |
| WO | WO-03070085 A2 | 8/2003 |
| WO | WO-03077726 A2 | 9/2003 |
| WO | WO-03090644 A1 | 11/2003 |
| WO | WO-03094744 A1 | 11/2003 |
| WO | WO-03094754 A1 | 11/2003 |
| WO | WO-03096851 A1 | 11/2003 |
| WO | WO-03101314 A1 | 12/2003 |
| WO | WO-03103548 A1 | 12/2003 |
| WO | WO-2004011037 A2 | 2/2004 |
| WO | WO-2004016186 A1 | 2/2004 |
| WO | WO-2004016299 A2 | 2/2004 |
| WO | WO-2004026153 A1 | 4/2004 |
| WO | WO-2004026371 A2 | 4/2004 |
| WO | WO-2004030547 A1 | 4/2004 |
| WO | WO-2004041148 A1 | 5/2004 |
| WO | WO-2004050138 A2 | 6/2004 |
| WO | WO-2004052178 A2 | 6/2004 |
| WO | WO-2004071312 A1 | 8/2004 |
| WO | WO-2004075741 A2 | 9/2004 |
| WO | WO-2004096012 A2 | 11/2004 |

| | | |
|---|---|---|
| WO | WO-2004096060 A2 | 11/2004 |
| WO | WO-2004098395 A1 | 11/2004 |
| WO | WO-2004103161 A2 | 12/2004 |
| WO | WO-2004110263 | 12/2004 |
| WO | WO-2005009257 | 2/2005 |
| WO | WO-2005056099 | 6/2005 |
| WO | WO-2005058239 | 6/2005 |
| WO | WO-2005089433 | 9/2005 |
| WO | WO-2006044797 | 4/2006 |
| WO | WO-2006055804 | 5/2006 |
| WO | WO-2006057702 | 6/2006 |
| WO | WO-2006072008 | 7/2006 |
| WO | WO-2006113394 | 10/2006 |

OTHER PUBLICATIONS

Abu-Rafea, B. et al. "Effect of body habitus and parity on insufflated $CO_2$ volume at various intraabdominal pressures during laparoscopic access in women," *Journal of Minimally Invasive Gynecology* (2006) 13, 205-210, Feb. 14, 2006.

Asao, T. et al. "Usefullness of a visceral mini-retractor accessible without trocar port during laparoscopic surgery," *Surgical Endoscopy* (1999) 13:91.

Landman, J. et al. "Application Of A Fixed Retractor System To Facilitate Laparosocopic Radical Prostatectomy," *American Urological Association*, vol. 171, 783-785, Feb. 2004.

Product Facts: Omni-Lapo Tract® Scope and Instrument Holder, Product Specifications, Omni-Tract® Surgical, 2005.

Székely, G. et al. "Anatomical Model Generation for Laparoscopic Surgery Simulation." In The Second Visible Human Project Conference Proceedings, Bethesda, MA: National Library of Medicine, Oct. 1998.

International Search Report and Written Opinion, PCT/US2008/084475, Jun. 10, 2010, 10 pages.

Partial International Search Report, PCT/US2008/074276, Dec. 18, 2008, 5 pages.

* cited by examiner

TISSUE RETRACTORS

FIELD OF THE INVENTION

The present invention relates to methods and devices for manipulating tissue during surgical procedures.

BACKGROUND OF THE INVENTION

During certain surgical procedures, body tissue such as organs can obstruct an area a surgeon needs accessible for surgery. Relocating the tissue during all or part of the procedure can allow a surgeon to access an otherwise obstructed part of the body. The tissue may also need to be relocated to reduce chances of it being damaged as work is being done on another, nearby part of the body.

Tissue retractors have been developed that allow some movement of tissue in a body cavity during a surgical procedure. For example, a tissue retractor may be inserted into the body through an incision, and it can be used to push tissue aside to provide access to an underlying area. Current retractors include a rigid fan-type design, a spoon or fork-like device, or an inflatable bladder. While such tissue retractors can move tissue, they typically move small amounts of tissue and are difficult or impossible to keep in a fixed position during use without constant human interaction. In addition, many known tissue retractors that are suitable for use with open surgical procedures are not well suited to minimally invasive procedures such as endoscopic procedures.

Accordingly, there remains a need for improved methods and devices for manipulating tissue.

SUMMARY OF THE INVENTION

The present invention generally provides tissue retractor devices as well as methods for performing various procedures using tissue retractors. The tissue retractors disclosed herein are particularly well suited for use with minimally invasive procedures (e.g., endoscopic, laparoscopic, and hand-assisted laparoscopic surgery ("HALS")) as they can be introduced through a small opening characteristic of minimally invasive surgery and can be reconfigured to effectively retract tissue during a surgical procedure. In one embodiment, a surgical retractor device is provided that includes a flexible fabric tissue retractor configured to support tissue. At least one grasping element can be coupled to a perimeter of the flexible fabric, and it can be configured to be manipulated to couple the flexible fabric to a surgical port, e.g., a trocar, inserted through a body wall and extending into a body cavity. The at least one grasping element can also be configured to move the flexible fabric and thereby move the tissue in a manner desired by a surgeon and/or required by a surgical procedure.

The flexible fabric of the device can have a variety of configurations, but in one embodiment at least one string is coupled to the fabric and configured to be manipulated to position tissue in a substantially fixed position with respect to the fabric. The flexible fabric can be configured to be inserted into the body cavity through the surgical port. In some embodiments, the surgical port is configured to be capable of receiving an instrument when the at least one grasping elements is coupled to the surgical port.

The at least one grasping element can also have a variety of configurations, such as one of an elliptical-shaped grommet, a clip, a wraparound tie, a hook, a magnetic clasp, and a clamp. In one embodiment, the at least one grasping element has a shape such that when a longitudinal axis of the at least one grasping element is oriented substantially parallel to a longitudinal axis of the surgical port, the at least one grasping element and the surgical port can become uncoupled. The at least one grasping element can also have a shape such that when a longitudinal axis of the at least one grasping element is oriented at a non-parallel and non-perpendicular angle to a longitudinal axis of the surgical port, the at least one grasping element anchors to the surgical port, thereby securing the flexible fabric to the surgical port in a fixed position.

In other aspects, one embodiment of a surgical method is provided and includes inserting a fabric into a body cavity in a first orientation, e.g., a roll. In some embodiments, the fabric can be inserted through a hand assisted laparoscopic surgery port. The method also includes configuring the fabric in a second orientation configured to retract tissue. The fabric can include at least one grasping element, and the method further includes coupling the at least one of the grasping element to a trocar inserted into the body cavity. The grasping element can be oriented on the trocar such that a longitudinal axis of the at least one grasping element is not parallel to a longitudinal axis of the trocar to secure the at least one grasping element to the trocar in a locked position and retract tissue.

In one embodiment, the method also includes positioning tissue in the fabric such that the fabric supports the tissue. Positioning tissue can include pulling at least one string coupled to the fabric to position tissue in a substantially fixed position with respect to the fabric. The at least once string can be slackened to release the tissue from the substantially fixed position with respect to the fabric.

In other aspects, the method can also include orienting the at least one grasping element on the trocar such that a longitudinal axis of the at least one grasping element is substantially parallel to a longitudinal axis of the trocar, thereby moving the at least one grasping element from the locked position to a position where the at least one grasping element can be removed from the trocar. In some embodiments, the method includes removing the trocar from the body cavity, thereby releasing the at least one grasping element from the trocar.

In another embodiment, a surgical method is provided that includes inserting a fabric through an incision to position the fabric in a body cavity and positioning tissue in the fabric such that the fabric supports the tissue. The method also includes manipulating at least one grasping element coupled to the fabric to attach the at least one grasping element to a trocar extending into the body cavity and anchoring the at least one grasping element to the trocar, thereby securing the fabric in a fixed position. Positioning tissue can include manipulating at least one string coupled to the fabric to move the fabric around the tissue. In other embodiments, positioning tissue in the fabric can include manipulating a grasper to grasp at least one of the tissue and the fabric to place the tissue in the fabric. Manipulating the at least one grasping element can include using a grasping device to couple the fabric to the trocar, and anchoring the at least one grasping element can include orienting a longitudinal axis of the at least one grasping element at a non-parallel and non-perpendicular angle with respect to a longitudinal axis of the trocar. In some embodiments, the at least one grasping element can be released from the trocar by removing the trocar from the body cavity. In other embodiments, the at least one grasping element can be released from the trocar by orienting a longitudinal axis of the at least one grasping element substantially parallel to a longitudinal axis of the trocar. The method can also include allowing an instrument to extend through the trocar when the grasping element is anchored to the trocar.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
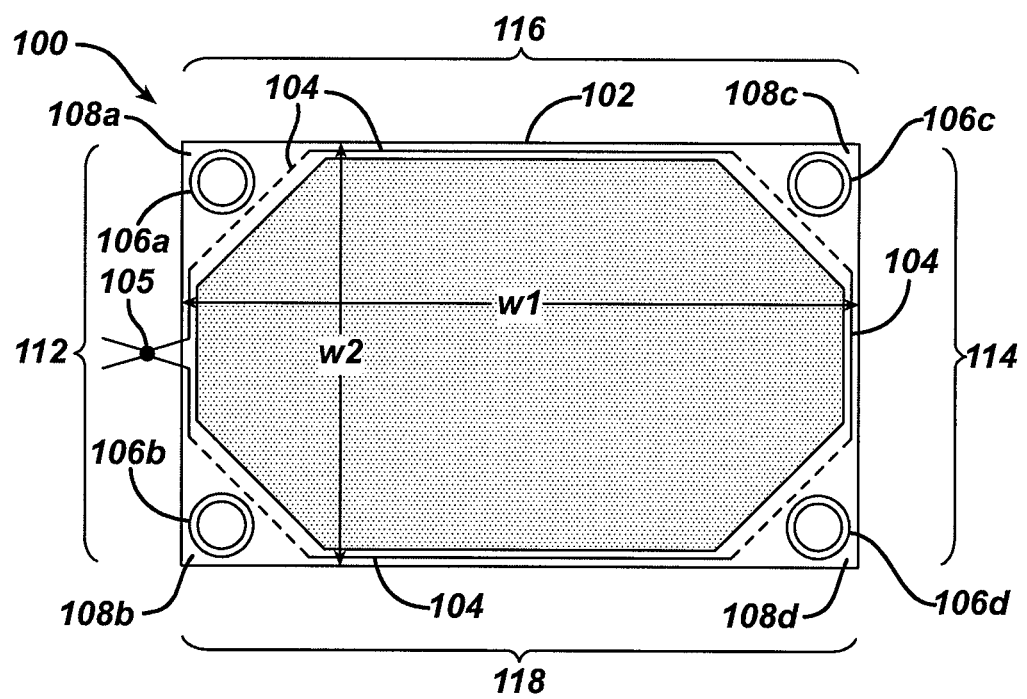
FIG. 1 is a schematic diagram of an embodiment of a retractor including grasping elements.

Certain exemplary embodiments will now be described to provide an overall understanding of the principles of the structure, function, manufacture, and use of the devices and methods disclosed herein. One or more examples of these embodiments are illustrated in the accompanying drawings. Those of skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for performing surgical procedures using tissue retractors. In general, the methods and devices allow a surgeon to use a retractor to capture a large or small amount of tissue in a fabric, to move the fabric to relocate the tissue to one or more convenient locations during the procedure, and to anchor the fabric and tissue in a substantially fixed position during a surgical procedure. The flexible nature of the fabric can allow the fabric to be moveable between an open position, in which the fabric can support tissue, and a closed position, in which the fabric can be folded, rolled, or otherwise compressed in size and fit through a relatively small port, e.g., a trocar or an incision in a tissue wall. Once the retractor is inside the body, the need to repeatedly position tissue during a procedure can be reduced because more than a small amount of tissue can be held in the fabric and moved at a time. The flexible nature of the fabric can allow more freedom of movement in positioning the fabric within the body and in moving the tissue rather than a retractor made of non-flexible material, such as metal. Additionally, holding and moving tissue in a fabric retractor can reduce the chances of the tissue slipping or sliding away from the retractor, a common occurrence when using rigid retractors. This also reduces the need for tissue reengaging and repositioning. Furthermore, the position of the fabric and thus the tissue held in the fabric can be easily anchored by coupling a trocar to one or more grasping elements coupled to a perimeter of the fabric, thereby reducing the chances of the fabric and thus any tissue it holds from slipping or sliding away from a desired position. Another feature of such a retractor is that it can be anchored and can maintain tissue in a desired location without the need for a surgeon to constantly hold and manipulate the retractor.

A person skilled in the art will appreciate that the devices disclosed herein can be used in numerous surgical procedures (including endoscopic, laparoscopic and HALS procedures), and in connection with numerous body cavities and body tissues. For example, the devices can be used in procedures that take place in the abdominal, thoracic, pelvic, and abdominopelvic cavities, and they can be used to move any tissue, including organs such as the bowel, small intestine, stomach, liver, uterus, etc. The devices can be introduced into the body in any way in any of the procedures, such as through an incision or percutaneously through an access device, such as a trocar or an endoscopic device.

A person skilled in the art will also appreciate that the particular configuration and materials of the retractor can vary depending on factors such as the type of procedure being performed and the type of tissue to be moved or relocated. The retractor can have any shape with any number of sides and curves, e.g., rectangular, elliptical, triangular, hexagonal, trapezoidal, etc. The retractor can also be made from any flexible fabric material appropriate for surgical use and can include zero, one, or more structural supports, e.g., ribs, inflatable bladders, etc. Grasping elements coupled to the retractor can be of any number and configuration on the fabric.

FIG. 1 illustrates one embodiment of a retractor 100 having a fabric 102 that can hold tissue during a surgical procedure. The substantially rectangular shaped fabric 102 as shown includes a pull string 104 and four grasping elements 106a, 106b, 106c, 106d. The pull string 104 is mated to or inlaid along a majority of the fabric's perimeter. The grasping elements 106a, 106b, 106c, 106d, shown here as grommets, are coupled to each of the fabric's four corners 108a, 108b, 108c, 108d, although the fabric 102 could include any number of grasping elements at any location on the fabric 102. Once inside the body, the fabric 102 can be manipulated to receive, hold, move, and release tissue by grasping and pulling (including tightening and slackening) one or more elements, such as the pull string 104 and/or the grommets 106a, 106b, 106c, 106d. Additionally, the fabric 102, and any tissue it supports, can be held in a substantially fixed position within the body by anchoring one or more of the grommets 106a, 106b, 106c, 106d to a port, as further described below.

The fabric 102 can have a variety of configurations that allow the fabric 102 to hold tissue and temporarily move tissue to another location during a surgical procedure. In the illustrated embodiment, the fabric 102 has a substantially rectangular shape having a first width w1 extending between shorter length sides 112, 114 that is greater than a second width w2 extending between longer length sides 116, 118. However, the fabric 102 can have any shape, e.g., rectangular (including square), elliptical (including circular), triangular, hexagonal, trapezoidal, etc. The fabric 102 can also have a two dimensional shape when in an open configuration as shown, but in other embodiments the fabric 102 can have a third dimension. For example, the fabric's shape in an open position can be cone-shaped, domed, elliptical (similar to a parachute), or prism-shaped with one or more sides of the prism missing so as to allow tissue to be held in the fabric 102.

The fabric 102 can also have a variety of sizes, and different sizes of the fabric 102 may be appropriate for relocation of different types of tissue, i.e., a larger fabric for moving the liver than for moving the stomach. Preferably, the fabric 102 has dimensions that allow it to fit inside a commercially available cannula so that, as further described below, the fabric 102 can be introduced into a body through the cannula.

The grasping elements 106a, 106b, 106c, 106d attached to the fabric 102 can also have any structure. For example, the grasping elements 106a, 106b, 106c, 106d can include any combination of grommets, clips, wraparound ties/loops, hooks, magnetic clasps, clamps, holes formed in the fabric 102, and other similar structures. The grasping elements 106a, 106b, 106c, 106d can have any shape, such as elliptical (including circular). The grasping elements 106a, 106b, 106c, 106d can also have any length and width. Preferably, the grasping elements 106a, 106b, 106c, 106d are of a shape compatible to fit around or otherwise couple to commercially available trocars, as further discussed below, thereby allowing the grasping elements 106a, 106b, 106c, 106d to be manipulated around the trocars when receiving, releasing, supporting, or moving tissue in the fabric 102.

As indicated above, the grasping elements 106a, 106b, 106c, 106d can be used to anchor the fabric 102 in a substantially fixed position. The grasping elements 106a, 106b, 106c, 106d can also be used for pulling the fabric 102 when introducing the fabric 102 into a body cavity, when receiving tissue in or releasing tissue from the fabric 102, and when moving tissue held in the fabric 102. Any number of grasping elements 106a, 106b, 106c, 106d can be coupled to the fabric 102 in any configuration, and the grasping elements 106a, 106b, 106c, 106d can be coupled to the fabric 102 at any point or points along its perimeter or elsewhere on its surface. Preferably, there are at least two grasping elements 106a, 106b, 106c, 106d coupled to the fabric 102 to provide adequate tension when using the grasping elements 106a, 106b, 106c, 106d in moving or securing the fabric 102. The grasping elements 106a, 106b, 106c, 106d can be mated to the fabric 102, or they can be integrally formed with the fabric 102. For example, FIG. 1 illustrates four individual grommets 106a, 106b, 106c, 106d, each mated to the fabric 102. For another example, the grasping elements 106a, 106b, 106c, 106d could include loops of fabric extending from one or more places along the fabric's perimeter. The grasping elements 106a, 106b, 106c, 106d are preferably permanently coupled to the fabric 102, but one or more of the grasping elements 106a, 106b, 106c, 106d can be removable.

The pull string 104 attached to the fabric 102 can also have any structure. For example, the pull string 104 can include any combination of threads, strings, ribbons, cords, rods, and other similar structures. The pull string 104 can include a loop of any size at one or more locations along its length such that fingers or surgical instruments can grasp the pull string 104 by engaging the loop. The pull string 104 can also have any length and width (in the case of the string being, for example, a ribbon).

Also as indicated above, the retractor 100 can include the pull string 104 to aid in positioning the fabric 102 and/or tissue supported by the fabric 102. The pull string 104 can also help in introducing the fabric 102 to a body cavity, as described further below. Any number of pull strings 104 can be coupled to the fabric 102 in any configuration, and the pull string 104 can be coupled to the fabric 102 at any point or points along the fabric's perimeter or elsewhere on its surface. The pull string 104 can also be coupled to one or more of the grasping elements 106a, 106b, 106c, 106d. The pull string 104 can include one or more individual strings. For example, as shown, one pull string is inlaid along a majority of the fabric's perimeter, but any number of individual pull strings can be coupled to the fabric 102. While the pull string 104 is not necessary, using the pull string 104 can make it easier to position the fabric 102 in a body cavity.

The pull string 104 can be coupled to the fabric 102 using various techniques. For example, as indicated above, the pull string 104 can be inlaid along a length of the fabric 102, possibly overhanging a portion of the fabric 102 as one or more tethers. In other embodiments, the pull string 104 can be integrally formed with the fabric 102, included as part of the fabric 102 (i.e., tethers of fabric extending from one or more places along the fabric's perimeter), or otherwise coupled to the fabric 102. As shown in FIG. 1, the pull string 104 can be coupled to the fabric 102 at one or more points but otherwise free along its length such that the pull string 104 can be pulled and cinched in position using a cinch 105, as described further below. The pull string 104 can be permanently coupled to the fabric 102, but in another embodiment, all or a portion of the pull string 104 can be removable from the fabric 102.

The fabric 102, the grasping elements 106a, 106b, 106c, 106d, and the pull string 104 can each be made from any type of biocompatible material appropriate for use in a body, such as mesh (braided or unbraided), fiber (natural or synthetic), gauze-like cloth, biocompatible metal, plastic, and other similar types of material. Moreover, the fabric 102 can be fluid pervious or impervious, and the material can be treated to increase or decrease its frictional interaction with tissue. Braided mesh is a useful material for the fabric 102 because tissue is generally less likely to stick or snag on braided mesh than on other materials. The fabric's perimeter can be made from the same or a different material from the fabric's internal area (shown shaded in FIGS. 1, 2, and 7). The internal area may be made from a more flexible material than the perimeter to provide more structural integrity to the fabric 102. The fabric 102 can include structural integrity elements such as ribs, described further below. In one embodiment, the pull string 104 is made from synthetic fiber, and the grasping elements 106a, 106b, 106c, 106d are made from a biocompatible metal. Each of the grasping elements 106a, 106b, 106c, 106d can be made from the same material, but one or more of the grasping elements 106a, 106b, 106c, 106d can be made from a material different from one or more of the other grasping elements 106a, 106b, 106c, 106d. The fabric 102 can also be flexible, thereby providing easy maneuverability when introducing the fabric 102 to a body cavity and when manipulating the fabric 102 once inside the body. The grasping elements 106a, 106b, 106c, 106d and the pull string 104 can be made from a non-elastic material, but they can be flexible or rigid.

Figure 2:
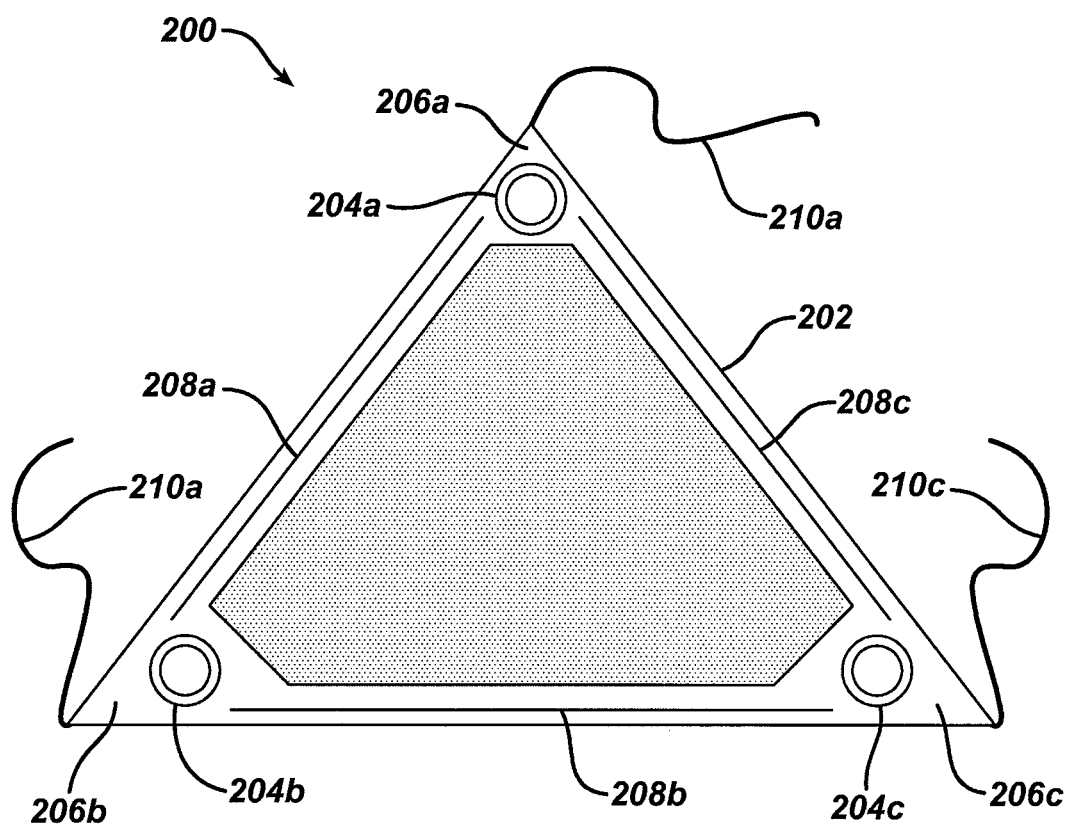
FIG. 2 is a schematic diagram of another embodiment of a retractor having a triangular shape and including grasping elements.

FIG. 2 illustrates another embodiment of a retractor 200 that includes a fabric 202 that can hold tissue during a surgical procedure. The retractor 200 is similar to the retractor 100 of FIG. 1 and includes three grasping elements 204a, 204b, 204c coupled to each of three corners 206a, 206b, 206c of the triangular shaped fabric 202. The fabric 202 also includes ribs 208a, 208b, 208c inlaid along a majority of the fabric's perimeter and three pull strings 210a, 210b, 210c coupled to each of the corners 206a, 206b, 206c. Each of the strings 210a, 210b, 210c overhang from the corners 206a, 206b, 206c as tethers. The fabric 202, the grasping elements 204a, 204b, 204c, and the pull strings 210a, 210b, 210c are similar to those described with reference to similarly named elements included in FIG. 1, and the retractor 200 can include variations as described herein for various retractors.

The retractor 200 can optionally include one or more structural members, such as the ribs 208a, 208b, 208c, that can provide structural integrity to the fabric 202, thereby making it easier for a surgeon to gather tissue in the fabric 202, for tissue to stay in the fabric 202 once received there, and/or for the fabric 202 to substantially maintain its shape when anchored as further discussed below. In an exemplary embodiment, the ribs 208a, 208b, 208c are made from a shape memory material, such as Nitinol (a nickel-titanium alloy), but they can be made from any type of material able to provide structure to the fabric 202 and appropriate for use in the body. Other exemplary metallic materials include alloys such as copper-zinc-aluminum-nickel, copper-aluminum-nickel, and nickel-titanium. Additional exemplary non-metallic materials may include thermoplastic materials such as Nylon or Nylon blends and shape memory polymers such as Veriflex™. The fabric 202 can include any number of the ribs 208a, 208b, 208c. The ribs 208a, 208b, 208c are shown as independent ribs in the illustrated embodiment, but the ribs 208a, 208b, 208c can include one or more interconnected ribs.

The ribs 208a, 208b, 208c can also have any configuration in the fabric 202. In the illustrated embodiment, the ribs 208a, 208b, 208c are coupled to the fabric 202 along a perimeter of the fabric 202. The ribs 208a, 208b, 208c can, however, be coupled to the fabric 202 in any configuration lengthwise, widthwise, and/or in one or more directions not parallel to any side of the fabric 202. The ribs 208a, 208b, 208c can also be coupled to the fabric's perimeter, in the fabric's interior, or both. If the ribs 208a, 208b, 208c are present, a majority of the fabric's perimeter preferably has ribs to reduce chances of tissue slipping or sliding out of the fabric 202.

The ribs 208a, 208b, 208c are typically inlaid in the fabric 202 as shown in FIG. 2, but the ribs 208a, 208b, 208c can be coupled to the fabric 202 in one or more other ways. For example, the ribs 208a, 208b, 208c can be sewn or otherwise mated to the fabric 202 such that the ribs 208a, 208b, 208c are fully or partially covered by the fabric 202. The ribs 208a, 208b, 208c can also be integrally formed on the fabric 202.

Figure 3:
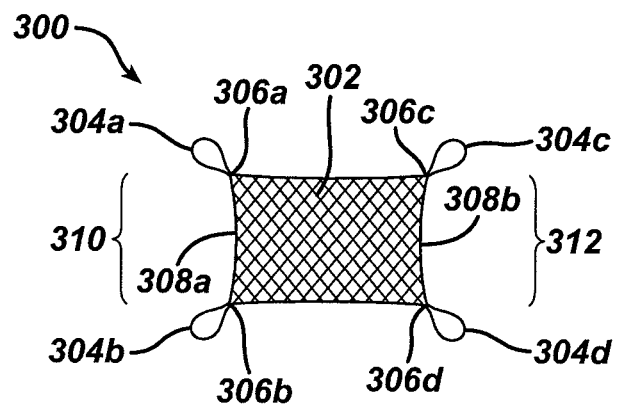
FIG. 3 is a schematic diagram of another yet embodiment of a retractor including grasping elements formed thereon.

FIG. 3 illustrates another embodiment of a retractor 300 that includes a fabric 302 that can hold tissue during a surgical procedure. The retractor 300 includes grasping elements 304a, 304b, 304c, 304d coupled to and extending from the fabric's corners 306a, 306b, 306c, 306d as loops integrally formed from the fabric 302. Material, e.g., metallic or non-metallic grommets, can be disposed within the loops 304a, 304b, 304c, 304d to provide more structural integrity to the loops 304a, 304b, 304c, 304d than would typically be provided by the fabric's material alone. Two strings 308a, 308b are coupled to the fabric 302 at its corners 306a, 306b, 306c, 306d and extend along opposing short sides 310, 312 of the fabric 302. The fabric 302, the grasping elements 304a, 304b, 304c, 304d, and the strings 308a, 308b are similar to those described with reference to similarly named elements included in FIG. 1, and the retractor 300 can include variations as described herein for various retractors.

Figure 4:
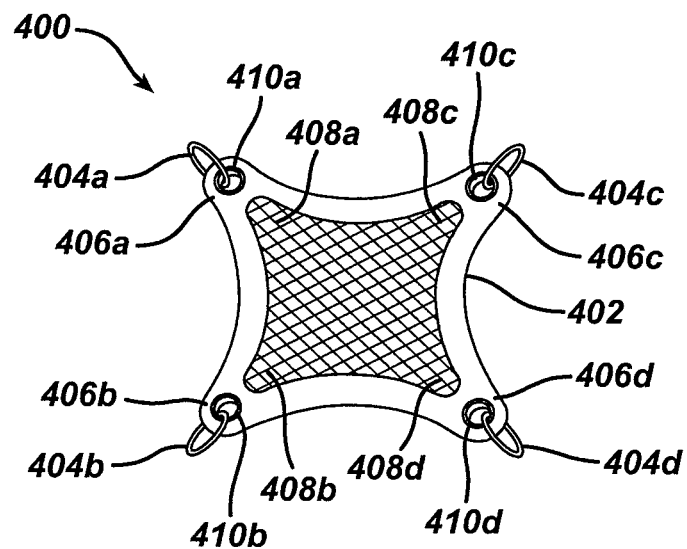
FIG. 4 is a schematic diagram of still another embodiment of a retractor including grasping elements coupled to openings formed thereon.

FIG. 4 illustrates still another embodiment of a retractor 400 that includes a fabric 402 that can hold tissue during a surgical procedure. The retractor 400 includes grasping elements 404a, 404b, 404c, 404d coupled to tabs 406a, 406b, 406c, 406d at each of the fabric's corners 408a, 408b, 408c, 408d. The fabric 302 and the grasping elements 404a, 404b, 404c, 404d are similar to those described with reference to similarly named elements included in FIG. 1, and the retractor 400 can include variations as described herein for various retractors.

In this embodiment, the tabs 406a, 406b, 406c, 406d each having an opening 410a, 410b, 410c, 410d that can be used to couple the grasping elements 404a, 404b, 404c, 404d to the fabric 402. The illustrated tabs 406a, 406b, 406c, 406d are coupled to the fabric 402 at the corners 408a, 408b, 408c, 408d of the rectangular shaped fabric 402, although the tabs 406a, 406b, 406c, 406d can be coupled to the fabric 402 at any location on the fabric 402 (preferably on the fabric's perimeter). Any number of tabs 406a, 406b, 406c, 406d can be coupled to the fabric 402 in any configuration, although the retractor 400 preferably includes at least two tabs 406a, 406b, 406c, 406d to provide adequate tension when moving or securing the fabric 402.

The tabs 406a, 406b, 406c, 406d and the openings 410a, 410b, 410c, 410d can have any shape and size (length, width, depth), but generally the shape and size is capable of receiving the grasping elements 404a, 404b, 404c, 404d, shown here as elliptical grommets, and allowing the grasping elements 404a, 404b, 404c, 404d to freely move within the openings 410a, 410b, 410c, 410d. Using a grasping element coupled to a tab can be particularly advantageous as it allows the grasping element to move with potentially more freedom of movement than a grasping element formed in a fabric, e.g., than if a tab is used as a grasping element (although the tabs 406a, 406b, 406c, 406d can be used as grasping elements).

Figure 5:
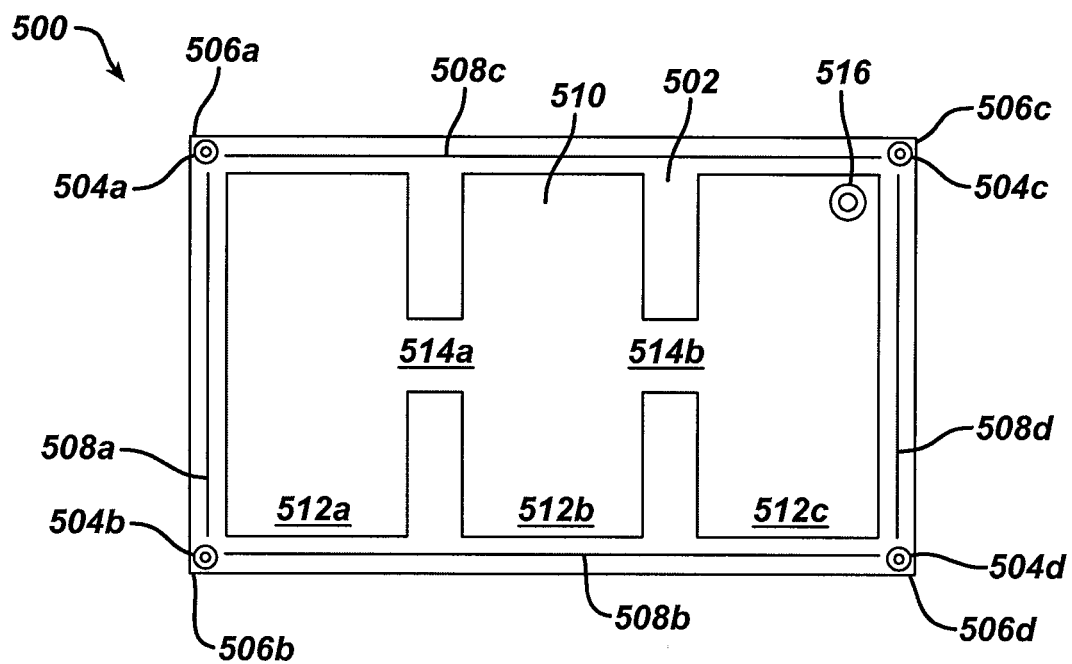
FIG. 5 is a schematic diagram of another embodiment of a retractor having several bladders formed therein.

FIG. 5 illustrates another embodiment of a retractor 500 that includes a fabric 502 that can hold tissue during a surgical procedure. The retractor 500 includes four grasping elements 504a, 504b, 504c, 504d coupled to each of four corners 506a, 506b, 506c, 506d of the substantially rectangular shaped fabric 502. The fabric 502 also includes ribs 508a, 508b, 508c, 508d inlaid along a majority of the fabric's perimeter. The fabric 502, the grasping elements 504a, 504b, 504c, 504d, and the ribs 508a, 508b, 508c, 508d are similar to those described with reference to similarly named elements discussed above. Although the retractor 500 is shown in FIG. 5 to be rectangular, it is understood that it can be a variety of alternative shapes.

In this embodiment, the fabric 502 includes a bladder 510 having a substantially rectangular shape with three substantially rectangular chambers 512a, 512b, 512c connected by two channels 514a, 514b, but the bladder 510 (and its chambers 512a, 512b, 512c and channels 514a, 514b) can have any shape. The bladder 510 can have any size, subject to the dimensions and flexibility of the fabric 502. If the bladder 510 includes more than one chamber and/or more than one channel, each chamber and each channel can have any size, different or the same from any other chamber or channel included in the bladder 510.

The bladder 510 can have a variety of configurations. For example, the bladder 510 can be formed in the fabric 502 as a cavity, e.g., two pieces of fabric can be mated together as discrete portions to create one or more cavities therein. The illustrated single cavity has three chambers 512a, 512b, 512c connected by two channels 514a, 514b, but the fabric 502 can include any number of bladders including one or more cavities connected by any number of channels (including zero channels). The left channel 514a connects the left chamber 512a with the middle chamber 512b, while the right channel 514b connects the middle chamber 512b with the right chamber 512c. In use, inflating fluid can be introduced into the bladder 510 through any one or more of the chambers 512a, 512b, 512c, and it can travel to one or more of the other chambers 512a, 512b, 512c via one or both of the channels 514a, 514b. Alternatively, the bladder 510 can include three unconnected cavities, and fluid can be separately introduced into each cavity to allow each cavity to be inflated to a selected size.

Fluid, such as air or saline (or any other gas or liquid), can be introduced to and drained from the bladder 510 through an inflation port 516 (e.g., a valve) formed in the fabric 502 and in communication with the bladder 510. In the illustrated embodiment, the right chamber 512c includes the inflation port 516 in one of its corners, but any of the chambers 512a, 512b, 512c could include the inflation port 516. Although the retractor 500 includes one inflation port 516, the tissue retractor 500 can include any number of inflation ports at any location on the fabric 502. If the tissue retractor 500 includes more than one bladder 510, each of the bladders 510 can have a dedicated inflation port 516. If the bladder 510 includes multiple chambers 512a, 512b, 512c, each bladder chamber 512a, 512b, 512c can have a dedicated inflation port 516 or, for chambers 512a, 512b, 512c connected by one or more channels 514a, 514b, there can be one inflation port 516 per two or more connected chambers 512a, 512b, 512c.

When the fabric 502 is inside a body and the bladder 510 is fully or partially inflated, the bladder 510 can provide increased rigidity to the fabric 502, thereby allowing the fabric 502 to more securely hold tissue and helping the fabric 502 to stay in a fixed position in the body. The bladder 510 also can be inflated to position tissue in the fabric 502. Because the fabric 502 includes the bladder 510, there can be a reduced need for other structural elements such as the ribs 508a, 508b, 508c, 508d, although one or more other structural elements such as the ribs 508a, 508b, 508c, 508d can be included in the retractor 500 to provide additional structural support to the fabric 502. When the bladder 510 is deflated, the fabric 502 can maintain a substantially flat configuration allowing the fabric 502 to be folded or otherwise compressed for easy introduction into, or removal out of, a body cavity.

Figure 6:
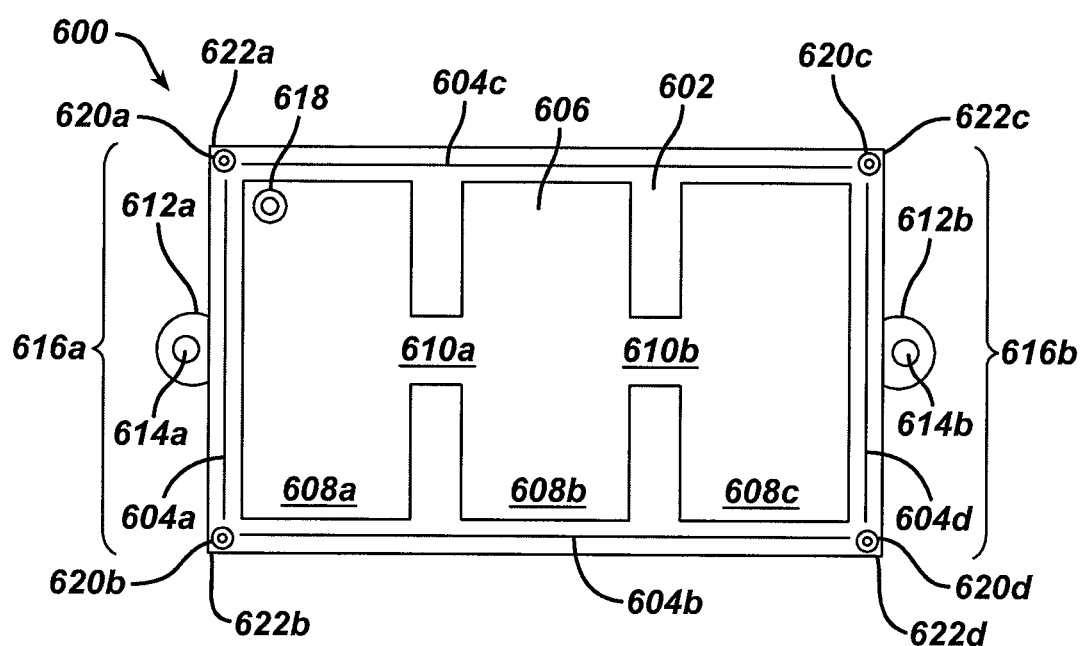
FIG. 6 is a schematic diagram of yet another embodiment of a retractor having tabs located thereon.

FIG. 6 illustrates another retractor 600 that includes a fabric 602 that can hold tissue during a surgical procedure. The retractor 600 includes ribs 604a, 604b, 604c, 604d inlaid along a majority of the fabric's perimeter and grommets 620a, 620b, 620c, 620d at the fabric's corners 622a, 622b, 622c, 622d. The fabric 602 also includes a bladder 606 having three chambers 608a, 608b, 608c connected by two channels 610a, 610b. The bladder 606 can be inflated through an inflation port 618. The fabric 602, the ribs 604a, 604b, 604c, 604d, and the bladder 606 (including the chambers 608a, 608b, 608c, the channels 610a, 610b, and the inflation port 618) are similar to those described with reference to similarly named elements discussed above.

In this embodiment, the retractor 600 includes tabs 612a, 612b that can be used in manipulating the fabric 602, each tab having an opening 614a, 614b. The tabs 612a, 612b and the openings 614a, 614b can have any shape and size (length, width, depth), but generally the shape and size is suitable for receiving a rigid tool, such as a commercially available rod. Use with a rigid tool is particularly advantageous as it allows the tool to be used to push the tabs, thereby pushing the retractor, as opposed to tethers which are used to pull the retractor. The illustrated tabs 612a-b are coupled to the fabric 602 at mid-portions of short sides 616a, 616b of the rectangular shaped fabric 602, although the tabs 612a, 612b can be coupled to the fabric 602 at any location on the fabric 602 (preferably on the fabric's perimeter). Any number of tabs 612a, 612b can be coupled to the fabric 602 in any configuration, although the retractor 600 preferably includes at least two tabs 612a, 612b to provide adequate tension when moving or securing the fabric 602 with rods. In use, each of the openings 614a, 614b can be capable of seating a rod or other grasping device for manipulating the fabric 602. Rods seated in the tabs 612a, 612b can be pushed or pulled to move the fabric 602 to a particular position to gather or position tissue. The tabs 612a, 612b can be used alone or in addition to other grasping elements such as tethers.

Figure 7:
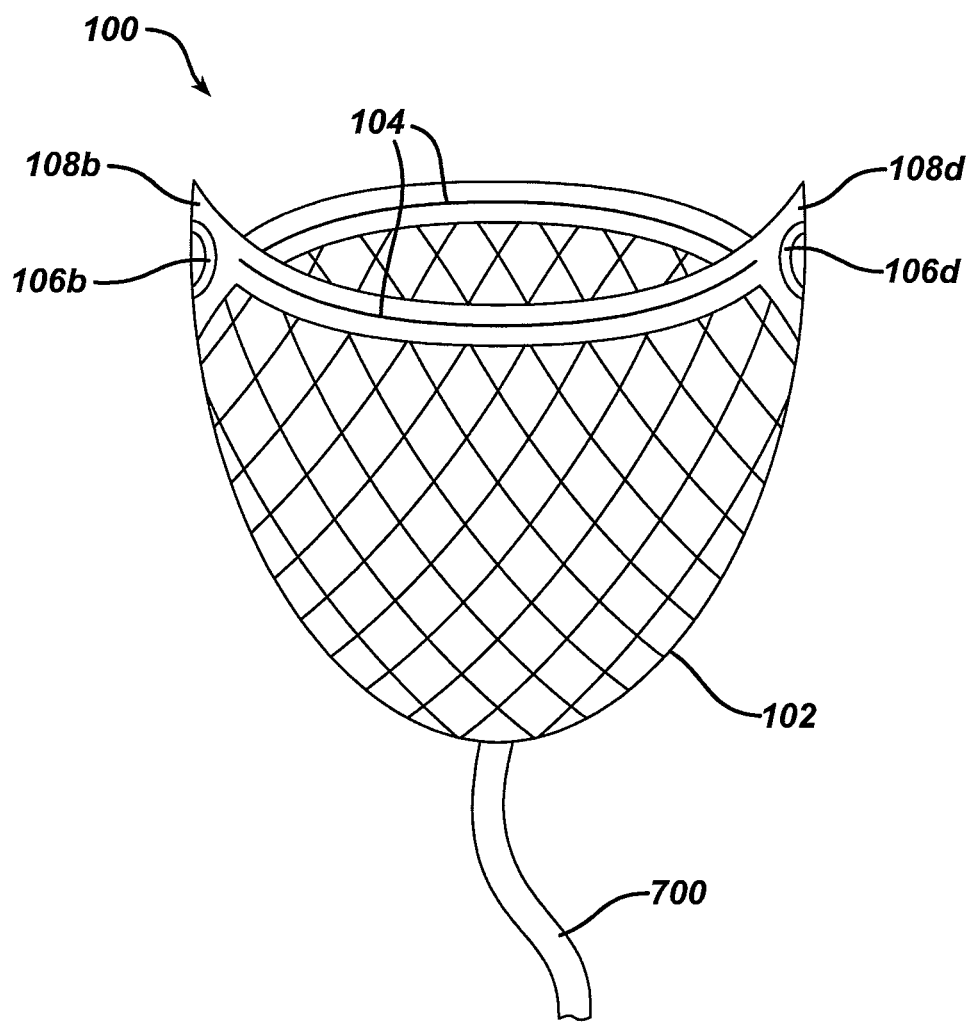
FIG. 7 is a perspective view of the retractor of FIG. 1 in a partially compressed position.

As indicated above, in use, the various retractors discussed herein can be moveable between an open position and a closed position. FIG. 7 illustrates the retractor 100 of FIG. 1 in a closed, partially compressed position. The retractor 100 is shown as if being held from above from the four corners 108a, 108b, 108c, 108d, with gravity "tenting" the fabric 102 in a downward direction and causing a deployment member 700 to dangle from a mid-portion of the underside of the fabric 102. In use, the fabric 102 can be pulled by the deployment member 700 into a body cavity through a port, such as an incision or a trocar. While the deployment member 700 is not necessary, using the deployment member 700 can make it easier to introduce the fabric 102 into a body cavity, particularly when the fabric 102 is introduced through a cannula.

The deployment member 700 can have any structure. For example, the deployment member 700 can be formed from threads, strings, ribbons, cords, rods, and other similar structures, or combinations thereof. The deployment member 700 can include a loop of any size at its terminal-most or free end or elsewhere along its length such that fingers or surgical instruments can grasp the deployment member 700 by engaging the loop. The deployment member 700 can also have any length and width. In one embodiment, the deployment member 700 should be long enough to extend out of a cannula, as further discussed below, when the fabric 700 is inside a cannula before introduction into a body.

Any number of deployment members 700 can be coupled to the fabric 102 in any configuration, but in an exemplary embodiment, the retractor 100 includes one deployment member 700. The deployment member 700 is preferably coupled to a mid-portion of the fabric 700 as shown on the retractor 100, but the deployment member 700 can be coupled to the fabric 102 at any location.

The deployment member 700 can be coupled to the fabric 102 in any way. For example, the deployment member 700 can be stitched to the fabric 102, included as part of the fabric 102 (i.e., ribbon of fabric extending from the fabric), or otherwise coupled to the fabric 102. The deployment member 700 can be permanently coupled to the fabric 102, but in another embodiment the deployment member 700 can be removable.

Figure 8:
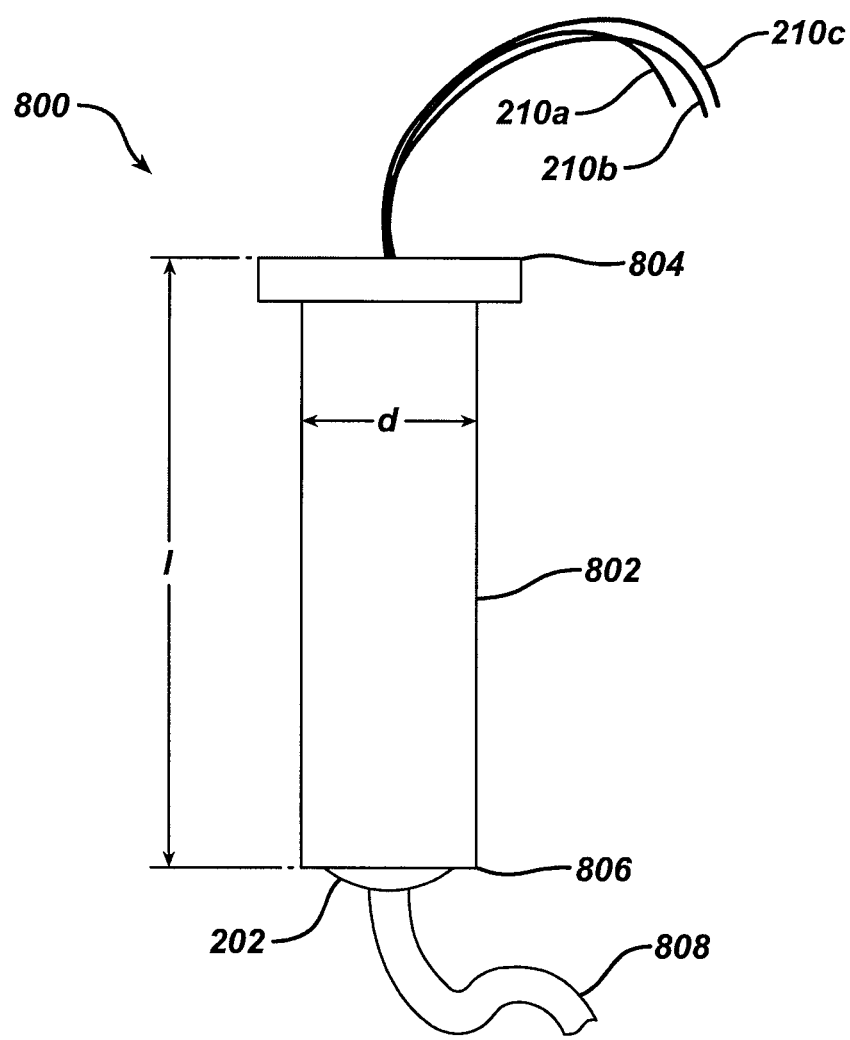
FIG. 8 is a side view of a cannula having the retractor of FIG. 2 disposed therein.

In one embodiment, in order to introduce a retractor into a body cavity, the retractor can be disposed within a cannula or other access port. FIG. 8 illustrates a retractor introduction system 800 that includes a cannula 802 having the retractor 200 of FIG. 2 (shown in FIG. 8 with a deployment member 808 coupled to the fabric's mid-portion) disposed therein between a proximal end 804 of the cannula 802 and a distal end 806 of the cannula 802. The cannula 802 can have any configuration. For example, the cannula 802 can be a trocar cannula configured to receive an obturator or any other access device that provides a pathway through tissue to a body cavity. The size of the cannula 802 can also vary. In one exemplary embodiment, the cannula 802 is substantially cylindrical.

As shown, the fabric 202 is in a closed position, e.g., folded, rolled, or otherwise compressed, to fit through the cannula 802. The fabric 202 can partially extend from the proximal and/or distal end 804, 806 of the cannula 802, but the fabric 202 is typically fully disposed in the cannula 802. Coupled to the fabric 202 and at least partially extending from the cannula 802 is the deployment member 808 and one or more of the strings 210a, 210b, 210c. When the fabric 202 is disposed in the cannula 802, the deployment member 808 extends from the distal end 806 of the cannula 802 such that the deployment member 808 can be pulled distally (e.g., by hand or another instrument separately accessing the site) to advance the fabric 202 out of the distal end 806 of the cannula 802 to allow the fabric 202 to support tissue. The fabric 202 can instead or in addition be advanced out of the distal end 806 of the cannula 802 by pushing on the strings 210a, 210b, 210c and/or the fabric 202 at the proximal end 804 of the cannula 802.

Figure 9:
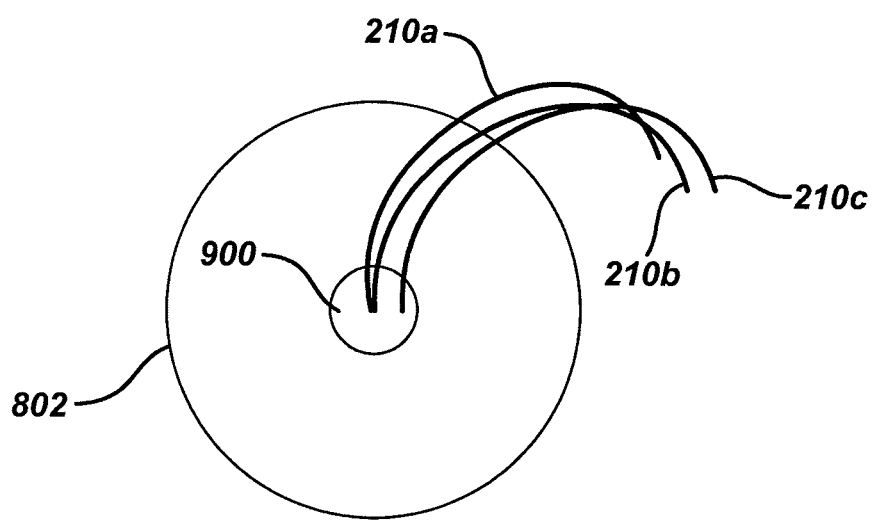
FIG. 9 is a top view of the retractor and cannula of FIG. 8.

As illustrated in FIG. 9, at least one of the strings 210a, 210b, 210c coupled to the fabric 202 can extend through an opening 900 from the proximal end 804 of the cannula 802 such that the strings 210a, 210b, 210c can be manipulated when the fabric 202 is advanced distally from the cannula 802 to hold tissue or move tissue supported by the fabric 202. The opening 900 can have any shape (e.g., elliptical, rectangular, etc.) and can be any size, although the opening 900 should be large enough to allow at least one of the strings 210a, 210b, 210c, if present, to extend from the proximal end 804 of the cannula 802.

Figure 10:
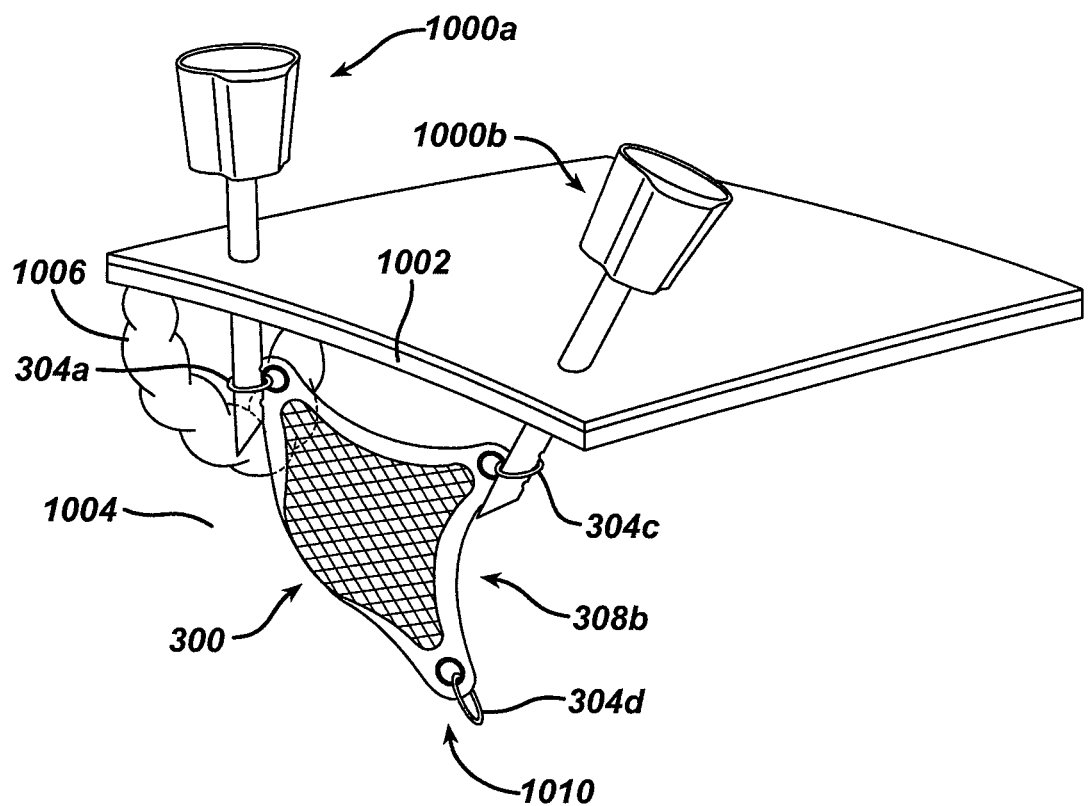
FIG. 10 is a perspective view of the retractor of FIG. 3 shown disposed in a body cavity.

With a retractor disposed in a cannula, the cannula can be introduced to a body cavity through a body wall, or the retractor can be introduced through a previously placed cannula. The retractor's fabric can then be pulled through the cannula and positioned in the body cavity where it can hold and/or move tissue. It is understood that the fabric can be introduced into the body in another way, such as directly through an incision. FIG. 10 illustrates first and second trocars 1000a, 1000b (e.g., the cannula 802 of FIG. 8) in use with the retractor 300 of FIG. 3 in a body cavity 1004 (e.g., the abdomen). Two trocars 1000a, 1000b are shown coupled to the retractor 300, but the retractor 300 can be coupled to any number of trocars. At least two trocars 1000a, 1000b are typically used to provide adequate tension in the fabric 302 when manipulating the retractor 300 to support tissue. Additionally, although the retractor 300 is shown, the illustrated methods using a trocar can be performed using any retractor disclosed herein or known in the art.

The trocars 1000a, 1000b can be inserted into the body cavity 1004 in a variety of ways, such as through an incision made in the body wall 1002. The trocars 1000a, 1000b can be at any angle relative to the body wall 1002 (e.g., perpendicular like the first trocar 1000a or at an angle like the second trocar 1000b) and may move horizontally and/or vertically during use. With at least one of the trocars 1000a, 1000b disposed in the body cavity 1002, the fabric 302 can be inserted into the body cavity 1004 through a disposed one of the trocars 1000a, 1000b by advancing the fabric 302 distally through the trocar.

The fabric 302 can be introduced into the body cavity 1004 in one orientation, e.g., in a closed position, but once partially or fully disposed in the body cavity 1004, the fabric 302 can be moved to another orientation, e.g., an open position, able to support a tissue 1006. When the fabric 302 is in the body cavity 1004, one or more of the grasping elements 304a, 304b, 304c, 304d can be used to couple to the trocars 1000a, 1000b, typically using one grasping element per trocar. Thus, one or more of the grasping elements 304a, 304b, 304c, 304d can be manipulated to help move and/or secure the fabric 402 (and any tissue it supports) from one state to a desired state, e.g., a substantially fixed position, as further described below.

Figure 11:
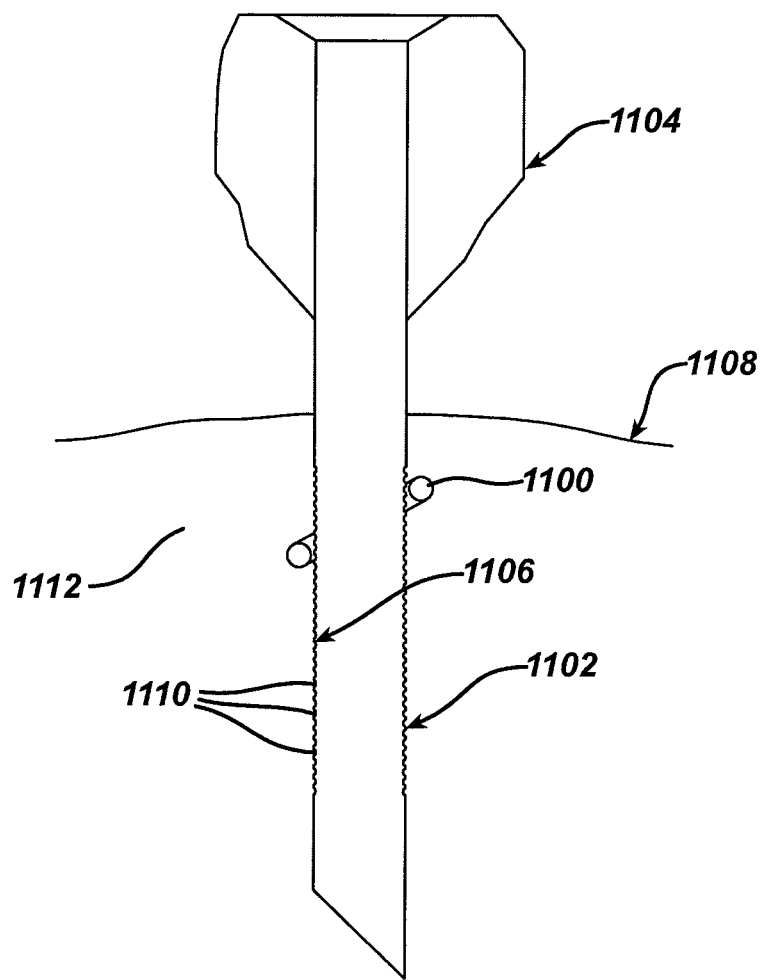
FIG. 11 is a cross-sectional schematic view of a trocar shown disposed through tissue.

The grasping elements 304a, 304b, 304c, 304d can couple to the trocars 1000a, 1000b in a variety of ways. Generally, the grasping elements 304a, 304b, 304c, 304d can each couple to an outside surface of an access port (such as the trocars 1000a, 1000b) inserted into the body cavity 1002. As illustrated in FIG. 11, when a grasping element 1100 (e.g., the grasping element 304c) is coupled to an outside surface 1102 of a trocar 1104 (e.g., the trocar 1000b), an inside surface 1106 of the trocar remains unobstructed to allow the trocar 1106 to receive an instrument that can extend from outside a body wall 1108 to inside a body cavity 1112.

Figure 12:
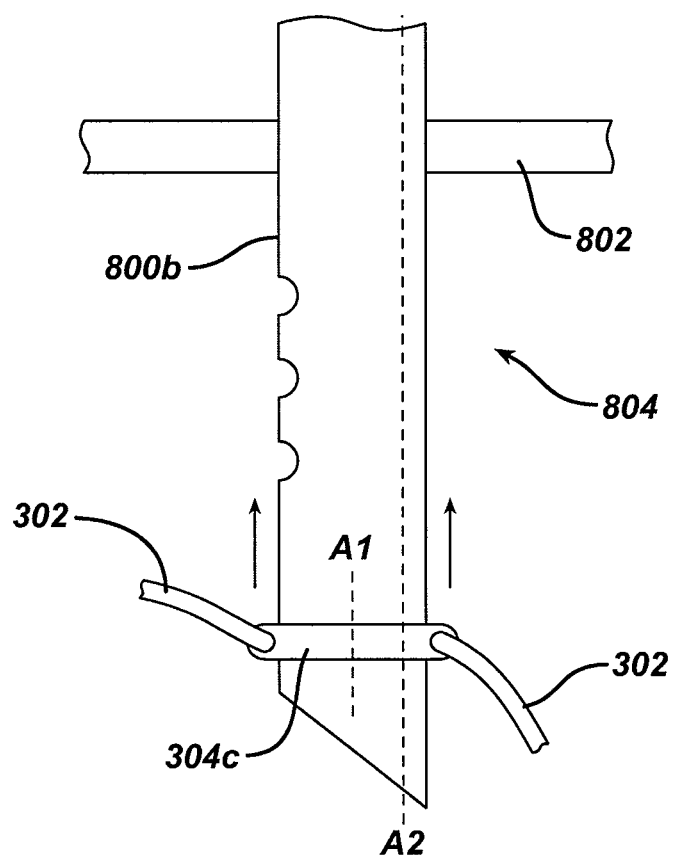
FIG. 12 is a schematic view of the retractor and the trocar of FIG. 10.
Figure 13:
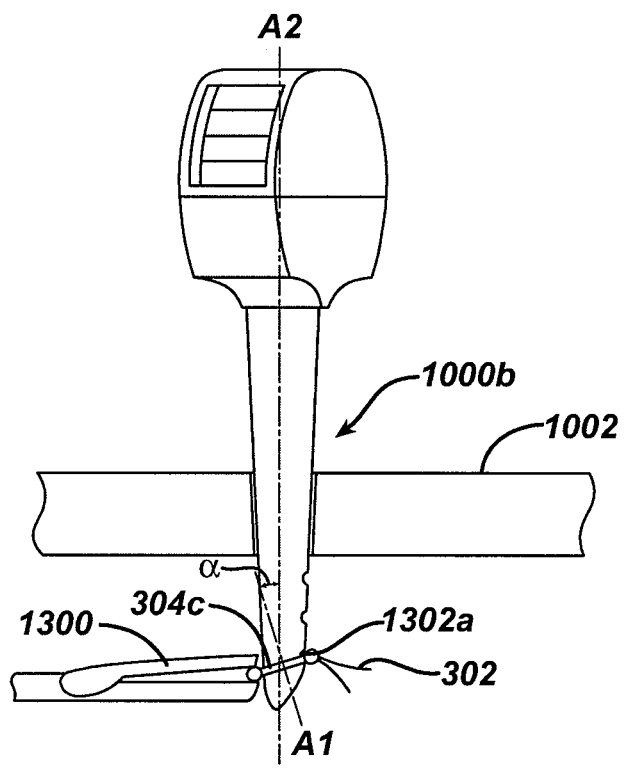
FIG. 13 is a perspective view of a grasper manipulating the retractor coupled to the trocar of FIG. 12.
Figure 15:
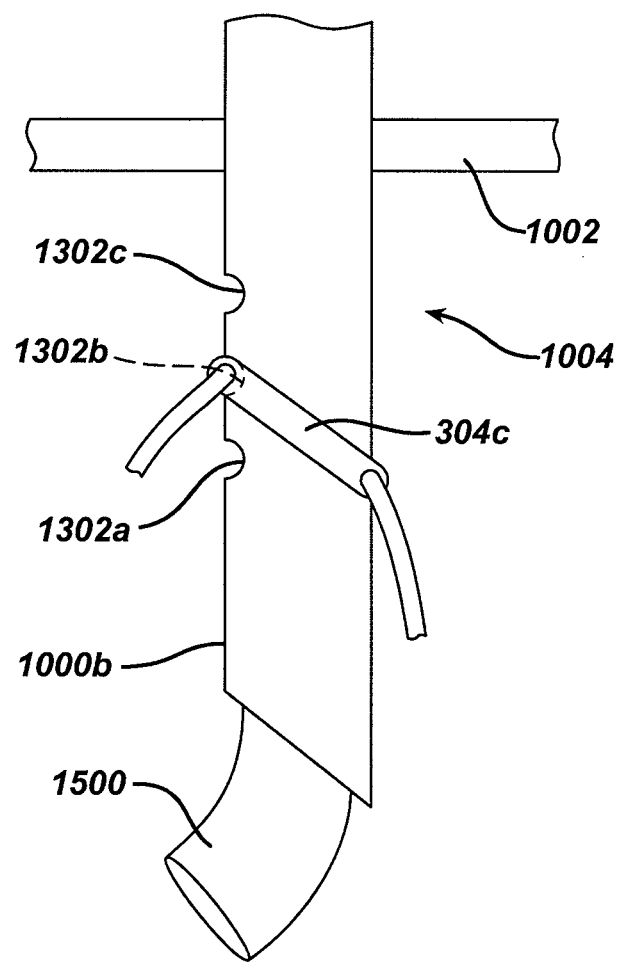
FIG. 15 is a schematic view of the retractor in a locked position on the trocar of FIG. 13.

One way that the grasping elements 304a, 304b, 304c, 304d can be anchored to the trocars 1000a, 1000b is shown in FIGS. 12-13 and 15. Although only one grasping element 304c is shown being coupled to one trocar 1000b, other grasping elements can be coupled to the same or other trocars in a similar manner. As shown in FIG. 10, the grommet 304c has a shape that allows it to be positioned around the trocar 1000b such that a longitudinal axis A1 of the grommet 304c is substantially parallel to a longitudinal axis A2 of the trocar 1000b. The grommet 304c can then be advanced proximally up the trocar 1000b, e.g., in the direction of the arrows from the body cavity 1004 toward the body wall 1002. A grasping device (grasper) 1300 (FIG. 13) can be used to manipulate the grommet 304c on the trocar 1000b. Examples of grasping devices include fingers and any tool suitable for surgical use and capable of grasping the material being grasped. Example of such tools include forceps (as shown in FIG. 13), rods, clips, spatulas, and other similar tools.

Figure 14:
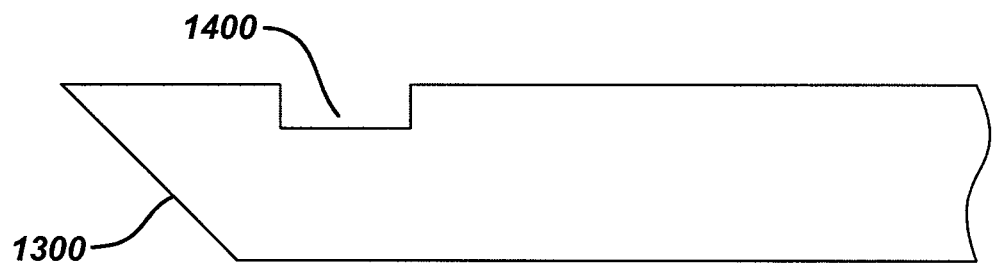
FIG. 14 is a schematic view of the grasper of FIG. 13.

The grasper 1300 can have any size and any configuration. FIG. 14 illustrates one embodiment of the grasper 1300 having a notch 1400 formed therein, which can be introduced to the site through another access port or incision. In use, the notch 1400 can capture and pull or otherwise manipulate elements such as the grasping elements 304a, 304b, 304c, 304d, the tissue 1006, the fabric 302, the strings 308a, 308b, a string cinch 1010, a deployment member, and/or any other elements coupled to the fabric 302. The grasper 1300 can also be used to capture one or more elements of the retractor 300 to help move the fabric 302 through the body wall 1002. The grasper 1300 can also manipulate the trocars 1000a, 1000b, although typically the grasper 1300 is used to manipulate the retractor 300. The notch 1400 has a rectangular shape in this example, but the notch 1400 can have any shape with linear and/or curved edges.

Once the grasping element 304c has been advanced on the trocar 1000b to a desirable position, the grasping element 304c can be released from the grasper 1300. Releasing the grasping element 304c can cause it to rotate on the trocar 1000b due to gravity and the weight of the fabric 302. The longitudinal axis A1 of the grasping element 304c can thereby be oriented at a non-parallel and non-perpendicular angle α to the longitudinal axis A2 of the trocar 1000b, as shown in FIG. 13. Alternatively or in addition to relying on gravity, the grommet 304c can be manipulated (e.g., with the grasper 1300) to form the angle α. The grommet 304c can be at least in part formed from a material (e.g., a high friction elastomeric material) to increase its friction holding capability with respect to the trocar 1000b. Alternatively or in addition, the grommet 304c can engage locking elements on the trocar 1000b such as grooves 1302a, 1302b, 1302c formed in the outside surface of the trocar 1000*b* to effectively lock the grommet 304*c* in position on the trocar 1000*b*. The grasping element 304*c* can include one or more locking support structures such as protrusions from or notches in its surface to help it engage the grooves 1302*a*, 1302*b*, 1302*c*.

Although the locking elements are shown as the grooves 1302*a*, 1302*b*, 1302*c* in this illustrated embodiment, the locking elements can have any structure. For example, the locking elements can including any combination of grooves, hooks, magnets, loops, ties, protrusions, and other similar structures. The locking elements' structure typically matches the structure of the retractor's grasping element(s), e.g., using magnets to engage magnetic grasping elements, using protrusions to engage clamps, or using hooks to engage grommets or loops. Any number of locking elements can be coupled to the trocar 1000*b* in any configuration, and the locking elements can include elements of any size at one or more locations along the trocar's length. The locking elements can also have any depth, width, and height. Additionally, each of the trocars 1000*a*, 1000*b* used with the retractor 300 can have any combination of the same or varying locking elements.

The locking elements can be coupled to the trocar 1000*b* using various techniques. For example, as shown in FIG. 13, the grooves 1302*a*, 1302*b*, 1302*c* are formed in the trocar 1000*b*. As another example, FIG. 11 shows a plurality grooves 1110 cut circumferentially around the outside surface 1102 of the trocar 1104. In other embodiments, the locking elements can be inlaid in or otherwise mated to the outer surface of the trocar 1000*b*. The locking elements can be included as part of a trocar's manufacture or can be retrofitted to an existing trocar. The locking elements can be made from any type of material appropriate for use in a body, such as the material of the grasping element 304*c* and the material of the trocar 1000*b*. The locking elements are preferably made from a non-elastic material, but they can be flexible or rigid.

With the grommet 304*c* anchored to the trocar 1000*b* in one of the grooves 1302*a*, 1302*b*, 1302*c*, the trocar 1000*b* can still be otherwise used in a surgical procedure (as the trocar 1000*b* also can before the grommet 304*c* couples to it). For example, an instrument, e.g., an endoscope 1500 shown in FIG. 15, can be inserted through the trocar 1000*b* to extend from outside the body wall 1002 to inside the body cavity 1004. For another example, another retractor could be inserted into the body cavity 1004 through the trocar 1000*b*.

Referring again to FIG. 10, once the fabric 302 has been introduced into the body cavity 1004, a surgeon can position the fabric 302 to hold the tissue 1006. Two of the grasping elements 304*a*, 304*c* have been anchored to the trocars 1000*a*, 1000*b* as described above, but the fabric 302 can be positioned to hold the tissue 1006, and the tissue 1006 can be supported by the fabric 302, before and/or after any number of the grasping elements 304*a*, 304*b*, 304*c*, 304*d* are coupled to the trocars 1000*a*, 1000*b*. In one embodiment, at least one of the grasping elements 304*a*, 304*b*, 304*c*, 304*d* is coupled to at least one of the trocars 1000*a*, 1000*b* before any tissue is positioned in the fabric 302 to provide increased structural integrity to the fabric 302 during the fabric 302 and/or the tissue 1006 positioning. The fabric 302 can hold any amount of the tissue 1006 and in any or all portions of the fabric 302. The tissue 1006 can include more than one type of tissue, thereby allowing one retractor to simultaneously move multiple types of tissue. The tissue 1006 can be held in more than one retractor, although only one retractor 300 is shown in the illustrated embodiment.

The tissue 1006 is shown positioned in the fabric 302 such that the fabric 302 supports the tissue 1006. The tissue 1006 can be positioned in the fabric 302 in a variety of ways that can be performed alone or in any combination. For example, positioning the tissue 1006 in the fabric 302 can include manipulating one of more of the strings 308*a*, 308*b* and/or any other elements coupled to the fabric 302 to move the fabric 302 around the tissue 1006. As another example, one or more of the grommets 304*a*, 304*b*, 304*c*, 304*d* can be adjusted vertically between any number of the grooves 1302*a*, 1302*b*, 1302*c*. One or more of the strings 308*a*, 308*b* and/or other elements can be simultaneously or sequentially pulled to position the tissue 1006 in the fabric 302 or to position the fabric 302 in a location proximate to the tissue 1006. Gravity can move the tissue 1006 from the proximate location to a position such that the tissue 1006 can be supported by the fabric 302. Additionally, the fabric 302 can include one or more structural elements such as ribs that can help position the tissue 1006 in the fabric 302.

In another example, the tissue 1006 can be positioned in the fabric 302 by manipulating a grasper (e.g., the grasper 1300 of FIGS. 13 and 14) to grasp at least one of the tissue 1006 and the fabric 302 to place the tissue 1006 in the fabric 302 or to place the fabric 302 around the tissue 1006. The grasper can grip the tissue 1006 or push the tissue 1006 to place it on or in a location proximate to the fabric 302.

Figure 16:
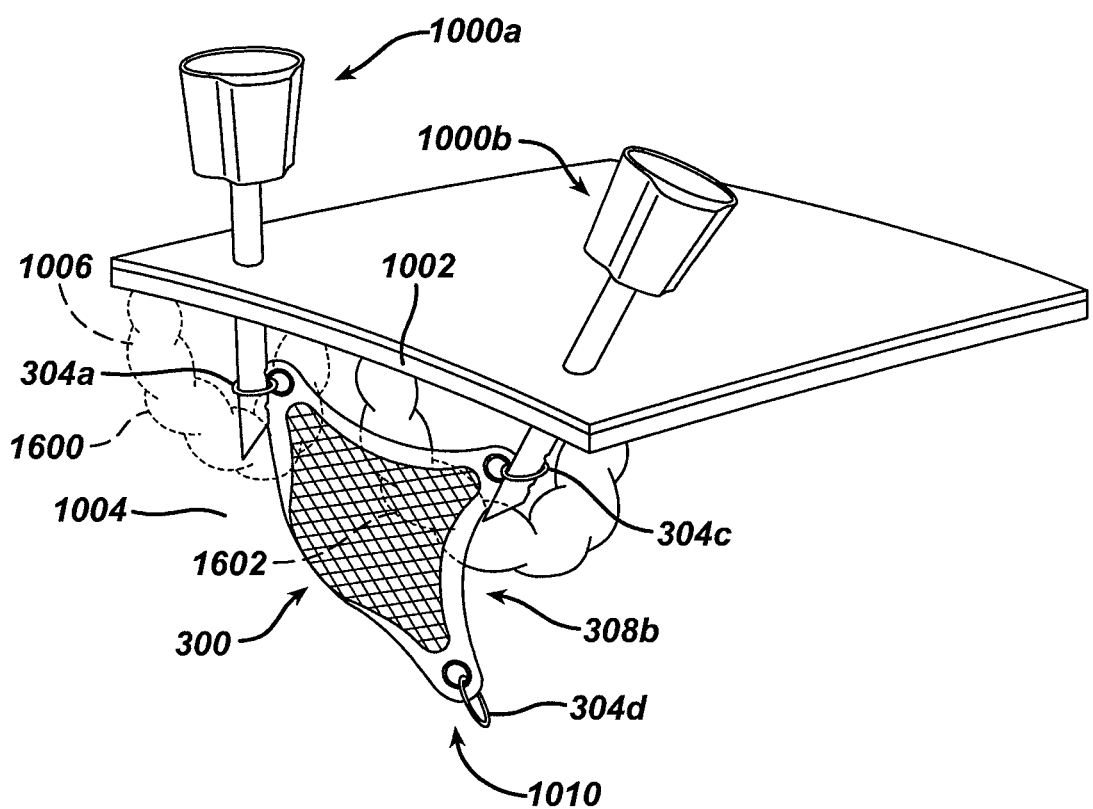
FIG. 16 is a perspective view of the retractor and trocar of FIG. 10 showing the retractor manipulated to move the tissue.

Once the fabric 302 supports a desired amount of the tissue 1006, the fabric 302 can be manipulated to move the tissue 1006. As shown in FIG. 16, the fabric 302 has been manipulated to move the tissue 1006 supported by the fabric 302. The tissue 1006 was moved from a first state 1600 (the tissue 1006 shown with dotted lines) to a second state 1602 (the tissue 1006 shown with solid lines). The first and second states 1600, 1602 are examples; the tissue 1006 can be moved in any direction and between any number of states during any one surgical procedure. Furthermore, the fabric 302 can also move between states corresponding to positions of the fabric 302 when the tissue 1006 is in its first and second states 1600, 1602, although as illustrated the fabric 302 is shown in the same position in FIGS. 10 and 16.

The tissue 1006 can be moved while supported by the fabric 302 in a variety of ways that can be performed alone or in combination. For example, manipulating the fabric 302 can include pulling at least one of the strings 308*a*, 308*b*, the string cinch 1010, the grasping elements 304*a*, 304*b*, 304*c*, 304*d*, a deployment member, and/or any other elements coupled to the fabric to move the fabric 402. In another example, a hand or a surgical tool (e.g., a grasper) may pull the fabric 402.

Once moved to a desired position such as the second state 1602, the fabric 302 can be fixed to anchor the fabric 302 and thus the tissue 1006 in a substantially fixed position. Fixing the fabric 302 can be accomplished by, for example, anchoring one or more of the grasping elements 304*a*, 304*b*, 304*c*, 304*d* to a trocar 1000*a*, 1000*b*, as described above, and/or pulling one or more of the strings 308*a*, 308*b* and engaging the string cinch 1010 for the pulled one or more of the strings 308*a*, 308*b*. Fixed in the second position 1602, the tissue 1006 can be held in that particular position with minimal or no human interaction during a surgical procedure. The fabric 302 can still be easily adjusted, e.g., by manipulating the grasping elements 304*a*, 304*b*, 304*c*, 304*d*, the strings 308*a*, 308*b*, by readjusting the cinch 1010, by pulling a deployment member, etc.

Once the tissue 1006 is held in a desired position by the fabric 302, the tissue 1006 and the fabric 302 can be maintained in that position with the help of the strings 308*a*, 308*b* and the string cinch 1010. For example, a surgeon can position the fabric 302 in a desirable location to receive or hold tissue, the string 308*b* can be pulled, and the cinch 1010 can be engaged, in addition to any of the grasping elements 304a, 304b, 304c, 304d locked to the trocars 1000a, 1000b, to help (temporarily) hold the fabric 302 in a substantially fixed position before or after the fabric 302 supports any of the tissue 1006.

The cinch 1010 can have any size and any configuration. In this example, the cinch 1010 is a spring-activated clamp, although any type of cinch 1010 can be used to capture and hold the respective ones of the strings 308a, 308b. A portion of the strings 308a, 308b themselves could be used as a cinch, e.g., by tying a knot. The cinch 1010 can be attached to the strings 308a, 308b before the fabric 302 introduced through a port to the body cavity 1004 or at any point after the fabric's insertion into the body cavity 1004. The cinch 1010 could also be used to hold any portion of the fabric 302 and any elements coupled to the fabric 302. Although only one cinch 1010 is shown in use in FIG. 16, any number of cinches can be used with any one tissue retractor, e.g., a separate cinch for each of the strings 308a, 308b. In this illustrated embodiment the cinch 1010 is located at one endpoint of each of the strings 308a, 308b, but one or more cinches can be disposed along any portion(s) of the strings 308a, 308b.

Figure 17:
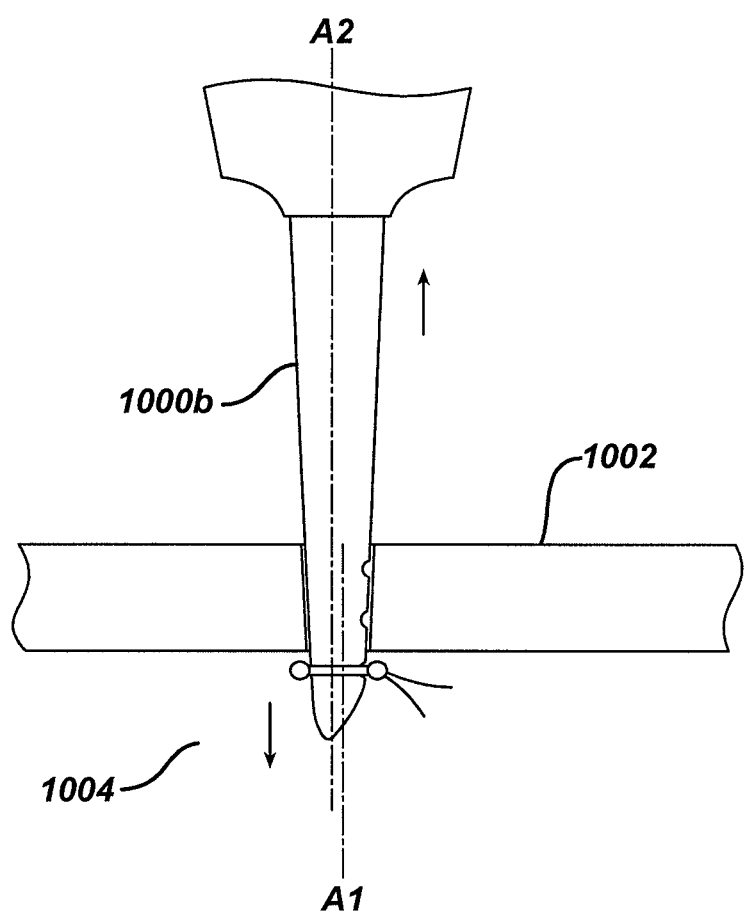
FIG. 17 is a perspective view showing the retractor being removed from the trocar of FIG. 15.

Some or all portions of the retractor 300 can be readjusted in the body cavity 1004 to reposition the fabric 302 and/or the tissue 1006 at any point during a surgical procedure. The strings 308a, 308b can be cut and/or the cinch 1010 can be released. Removing the trocars 1000a, 1000b by proximally pulling them out of the body cavity 1004 and through the body wall 1002 allows any grasping elements 304a, 304b, 304c, 304d coupled to them to be released. For example, as shown in FIG. 17, proximally pulling the trocar 1000b with the grommet 304c locked in position on it (e.g., as shown in FIG. 13) brings the grommet 304c into contact with an interior surface of the body wall 1002. The contact can cause the grommet 304c to rotate up against the body wall 1002 such that the longitudinal axis A1 of the grommet 304c can be oriented substantially parallel to the longitudinal axis A2 of the trocar 1000b. With the axes A1, A2 parallel, the grommet 304c can be released from the trocar 1000b in a distal direction, thereby discharging the grommet 304c into the body cavity 1004. The trocar 1000b can remain partially disposed in the body cavity 1004 after the grommet 304c has been released. Alternatively or in addition to pulling the trocar 1000b to release the grommet 304c, a grasping element (e.g., the grasper 1300 of FIGS. 13 and 14) can be used in removing the grommet 304c from the trocar 1000b. When the retractor 300 is no longer coupled with any of the trocars 1000a, 1000b, the retractor 300 can be removed from the body cavity 1004 through a port, such as one of the trocars 1000a, 1000b or a hand port.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new and/or used instrument(s) is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims.

What is claimed is:

1. A surgical retractor device, comprising:
    a surgical port having an elongate shaft configured to be inserted through a body wall and extend into a body cavity;
    a flexible fabric configured to support tissue; and
    at least one grasping element coupled to a perimeter of the flexible fabric and configured to be manipulated to couple the flexible fabric to the elongate shaft of the surgical port, and configured to move the flexible fabric and thereby move the tissue, wherein
    the at least one grasping element has a shape such that when a longitudinal axis of the at least one grasping element is oriented substantially parallel to a longitudinal axis of the elongate shaft of the surgical port, the at least one grasping element and the surgical port can become uncoupled,
    the at least one grasping element has a shape such that when a longitudinal axis of the at least one grasping element is oriented at a non-parallel and non-perpendicular angle to the longitudinal axis of the elongate shaft of the surgical port, the at least one grasping element anchors to the surgical port, thereby securing the flexible fabric to the surgical port in a fixed position, and
    when the longitudinal axis of the at least one grasping element is oriented substantially parallel to the longitudinal axis of the elongate shaft of the surgical port, the at least one grasping element can slide along the elongate shaft and can slide off a distal end of the elongate shaft to become uncoupled from the surgical port, and when the longitudinal axis of the at least one grasping element is oriented at the non-parallel and non-perpendicular angle to the longitudinal axis of the elongate shaft of the surgical port, the at least one grasping element cannot slide along the elongate shaft.

2. The device of claim 1 wherein the surgical port comprises a trocar.

3. The device of claim 1, wherein the flexible fabric is configured to be inserted into the body cavity through the surgical port.

4. The device of claim 1, wherein the surgical port is configured to be capable of receiving an instrument when the at least one grasping elements is coupled to the surgical port.

5. The device of claim 1, further comprising at least one string coupled to the fabric and configured to be manipulated to position tissue in a substantially fixed position with respect to the fabric.

6. The device of claim 5, wherein the string is located in the perimeter of the flexible fabric surrounding an internal area of the flexible fabric.

7. The device of claim 1, wherein the at least one grasping element comprises one of an elliptical-shaped grommet, a tab, a fabric loop, a clip, a wraparound tie, a hook, a magnetic clasp, and a clamp.

8. The device of claim 1, wherein the surgical port comprises a hand assisted laparoscopic surgery port.

9. The device of claim 1, wherein the flexible fabric is configured to be rolled such that the flexible fabric can be inserted as a roll into the body cavity through the surgical port inserted through the body wall.

10. The device of claim 1, further comprising a deployment member coupled to the flexible fabric.

11. The device of claim 10, wherein the deployment member is coupled to a mid-portion of the flexible fabric.

12. The device of claim 1, wherein the at least one grasping element comprises a plurality of grasping elements located symmetrically around the perimeter of the flexible fabric.

13. The device of claim 1, wherein an internal area of the flexible fabric is formed of a more flexible material than a material forming the perimeter of the flexible fabric.

14. The device of claim 1, wherein the elongate shaft of the surgical port includes at least one locking element configured to engage the at least one grasping element and secure the flexible fabric to the surgical port in the fixed position when the longitudinal axis of the at least one grasping element is oriented at the non-parallel and non-perpendicular angle to the longitudinal axis of the elongate shaft of the surgical port.

15. The device of claim 14, wherein the at least one locking element comprises one of a hook, a magnet, a loop, a tie, and a protrusion.

16. The device of claim 1, wherein the at least one grasping element has an elliptical shape, and the elongate shaft of the surgical port has a cylindrical shape.

17. A surgical retractor device, comprising:
   a surgical port having an elongate shaft configured to be inserted through a body wall and extend into a body cavity;
   a flexible fabric configured to support tissue; and
   at least one grasping element coupled to a perimeter of the flexible fabric and configured to be manipulated to couple the flexible fabric to the elongate shaft of the surgical port, and configured to move the flexible fabric and thereby move the tissue, wherein
   the at least one grasping element has a shape such that when a longitudinal axis of the at least one grasping element is oriented substantially parallel to a longitudinal axis of the elongate shaft of the surgical port, the at least one grasping element and the surgical port can become uncoupled,
   the at least one grasping element has a shape such that when a longitudinal axis of the at least one grasping element is oriented at a non-parallel and non-perpendicular angle to the longitudinal axis of the elongate shaft of the surgical port, the at least one grasping element anchors to the surgical port, thereby securing the flexible fabric to the surgical port in a fixed position,
   the elongate shaft of the surgical port includes at least one locking element configured to engage the at least one grasping element and secure the flexible fabric to the surgical port in the fixed position when the longitudinal axis of the at least one grasping element is oriented at the non-parallel and non-perpendicular angle to the longitudinal axis of the elongate shaft of the surgical port, and
   the at least one locking element comprises a plurality of grooves formed in the elongate shaft of the surgical port, the at least one grasping element being configured to slide along the elongate shaft when the longitudinal axis of the at least one grasping element is oriented at the non-parallel and non-perpendicular angle to the longitudinal axis of the elongate shaft of the surgical port, and being configured to engage a selected one of the grooves when the longitudinal axis of the at least one grasping element is oriented at the non-parallel and non-perpendicular angle to the longitudinal axis of the elongate shaft of the surgical port to secure the flexible fabric to the surgical port in the fixed position.

18. The device of claim 17, wherein
   the perimeter of the flexible fabric is made from a less flexible material than an internal area of the flexible fabric surrounded by the perimeter.

* * * * *